(12) United States Patent
Mithen et al.

(10) Patent No.: US 11,685,959 B2
(45) Date of Patent: Jun. 27, 2023

(54) GENETIC MARKERS FOR MYB28

(71) Applicants: SEMINIS VEGETABLE SEEDS, INC., St. Louis, MO (US); PLANT BIOSCIENCE LIMITED, Norwich (GB)

(72) Inventors: Richard F. Mithen, Norwich (GB); Maria Traka, Norwich (GB); Bart W. Brugmans, Beek en Donk (NL)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 310 days.

(21) Appl. No.: 16/601,502

(22) Filed: Oct. 14, 2019

(65) Prior Publication Data

US 2020/0172986 A1 Jun. 4, 2020

Related U.S. Application Data

(62) Division of application No. 15/359,471, filed on Nov. 22, 2016, now Pat. No. 10,472,685, which is a division of application No. 14/025,737, filed on Sep. 12, 2013, now Pat. No. 9,567,650.

(60) Provisional application No. 61/700,731, filed on Sep. 13, 2012.

(51) Int. Cl.
  *C12Q 1/68* (2018.01)
  *C12N 15/82* (2006.01)
  *C12Q 1/6895* (2018.01)

(52) U.S. Cl.
  CPC ....... *C12Q 1/6895* (2013.01); *C12N 15/8241* (2013.01); *C12N 15/8243* (2013.01); *C12Q 2600/13* (2013.01); *C12Q 2600/156* (2013.01); *C12Q 2600/158* (2013.01)

(58) Field of Classification Search
  None
  See application file for complete search history.

(56) References Cited

U.S. PATENT DOCUMENTS

| | | |
|---|---|---|
| 5,492,547 A | 2/1996 | Johnson |
| 6,340,784 B1 | 1/2002 | Mithen et al. |
| 8,492,616 B2 | 7/2013 | Mero |
| 9,096,863 B2 | 8/2015 | Geu-Flores |
| 9,248,474 B2 | 2/2016 | Teramoto et al. |
| 9,567,650 B2 | 2/2017 | Mithen et al. |
| 9,617,554 B2 | 4/2017 | Van Den Bosch et al. |
| 10,385,353 B2 | 8/2019 | van den Bosch et al. |
| 10,472,685 B2 | 11/2019 | Mithen et al. |
| 10,982,220 B2 | 4/2021 | van den Bosch et al. |
| 2010/0011462 A1 | 1/2010 | Kliebenstein |
| 2011/0016582 A1* | 1/2011 | Geu-Flores ........ C12N 15/8243 435/254.2 |

FOREIGN PATENT DOCUMENTS

| | | |
|---|---|---|
| EP | 1069819 | 7/2002 |
| JP | 2011-97921 | 5/2011 |
| WO | WO 99/052345 | 10/1999 |
| WO | WO 2010/001119 | 1/2010 |
| WO | WO 2011/158759 | 12/2011 |

OTHER PUBLICATIONS

Hirani, 2011, QTL Mapping, Gene Identification and Genetic Manipulation of Glucosinolates in *Brassica rapa* L., PhD Thesis, University of Manitoba, pp. 1-164, published Jul. 2011.*
Mithen et al., 2003, Development of isothiocyanate-enriched broccoli, and its enhanced ability to induce phase 2 detoxification enzymes in mammalian cells, Theor. Appl. Genet. 106: 727-734.*
Joseph et al., 2015, Genetic Variation in the Nuclear and Organellar Genomes Modulates Stochastic Variation in the Metabolome, Growth, and Defense, PLoS Genet 11(1): e1004779.doi:10.1371/journal.pgen.1004779.*
Bisht et al., 2009, Fine mapping of loci involved with glucosinolate biosynthesis in oilseed mustard (*Brassica juncea*) using genomic information from allied species, Theor. Appl. Genet. 118: 413-421.*
U.S. Appl. No. 17/175,280, filed Feb. 12, 2021, van den Bosch et al.
USPTO: Non-Final Office Action regarding U.S. Appl. No. 16/431,310 dated Mar. 23, 2020.
U.S. Appl. No. 16/431,310, filed Jun. 4, 2019, van den Bosch.
Anonymous, "About Beneforte," Beneforte Super Broccoli, IFR Institute of Food Research, pp. 1-3, accessed on Jan. 25, 2016 from <<http://www.superbroccoli.info/about-beneforte/timelines>>.
Apio, Inc. is proud to introduce Eat Smart® Beneforté® broccoli, http://www.eatsmartbeneforte.com, undated.
Associate website for Beneforte broccoli, <http://www.benforte.com/>, dated Aug. 2, 2011.
Augustine et al. (*J of Experimental Botany*; 64:4907-4921; 2013.

(Continued)

*Primary Examiner* — Medina A Ibrahim
(74) *Attorney, Agent, or Firm* — Dentons US LLP; Michelle Samonek

(57) ABSTRACT

The present invention relates to a method for determining the genotype of a Cruciferous vegetable plant for a plant with an increased glucosinolate level, comprising obtaining a sample of nucleic acids from said plant or a portion thereof and detecting in said nucleic acids a polymorphism at the Myb28 locus that is genetically linked to an increased glucosinolate level. The polymorphism may comprises at least one of: a) a single nucleotide polymorphism (SNP) at a position corresponding to nucleotide 83, 136, 226, 563, 610, 830, 995, 1116, 1513, 1577, 1606, 1620, 1825, 1863, 1877 or 2026 of SEQ ID NO: 1, or b) a polymorphism in the number of nucleotides present between nucleotides 323 and 332, between nucleotides 521 and 524, between nucleotides 783 and 786, between nucleotides and 909 and 914, between nucleotides 1365 and 1369, between 1811 and 1821, or between nucleotides 2046 and 2056 of SEQ ID NO: 1, or c) a polymorphism in the number of nucleotides present between nucleotides 836 and 837, between nucleotides 867 and 868, or between nucleotides 943 and 944 of SEQ ID NO: 1.

21 Claims, 10 Drawing Sheets

Specification includes a Sequence Listing.

(56) References Cited

OTHER PUBLICATIONS

Batley et al., "SNP Applications in Plants, from Association Mapping in Plants," pp. 95-101; 2007.
Bellostas et al., *Scientia Horticulturae* 114:234-242; 2007.
Bisht et al., "Fine mapping of loci involved with glucosinolate biosynthesis in oilseed mustard (*Brassica juncea*) using genomic information from allied species," *Theor Appl Genet* 118:413-421, 2009.
Bouhoun, et al., "Alignment of the conserved C genomes of *Brassica oleracea* and *Brassica napus*," *Theor. Appl. Genet.*; 93:833-839, 1996.
Cheng et al., "Research Progress on Regulation and Synthesis Genes on Glucosinolates Biosynthesis in Crucifer," China Vegetables 12:1-6, 2010.
Cheng et al., "BRAD, the genetics and genomics database for *Brassica* plants," *BMC Plant Biology*; 11:136, 2011.
Cheng, "Study in the relationship between Glucosinolate content and Regulation and Synthesis Gene Expression in Cabbage," Chinese Master Thesis, Agricultural Science and Technology Series No. 2; published on Feb. 15, 2011.
Christie, "Better Broccoli," *Produce Processing* pp. 1-3, 2010, available at <<http://produceprocessing.net/article/better-broccoli/>>.
Crowhurst, "Dutch seed open days—widening the field," *Horticulture Week* online article, available at <http://www.hortweek.com/Edibles/article/1099235/dutch-seedopendays-widening-field/>, dated Oct. 21, 2011.
EBI Accession No. ARA20191, "Thale cress Myb29 amplifying PCR primer, MYB29 f.", May 1, 2008.
EBI Accession No. HD429246, "Sequence 305962 from Patent EP2213738," Aug. 18, 2010.
GenBank Accession No. AB671773, dated Apr. 20, 2012.
GenBank Accession No. AC232495, dated Sep. 11, 2008.
GenBank Accession No. AF399834, dated Dec. 17, 2003.
GenBank Accession No. CP002688.1, dated Jun. 16, 2011.
GenBank Accession No. FJ584288, dated Aug. 12, 2009.
GenBank Accession No. FJ584289, published Aug. 12, 2009.
GenBank Accession No. GQ478992, dated Apr. 4, 2011.
GenBank Accession No. HQ270468, dated Nov. 29, 2010.
Gigolashvili et al., "The R2R3-MYB transcription factor HAG1/MYB28 is a regulator of methionine-derived glucosinolate biosynthesis in *Arabidopsis thaliana*," *The Plant Journal* 51:247-261, 2007.
Harper et al., "Associative transcriptomics of traits in the polyploid crop species *Brassica napus*," *Nature Biotechnology* 30(8):798-802, 2012.
Hirani, "QTL Mapping, Gene Identification and Genetic Manipulation of Glucosinolates in *Brassica rapa* L.," Doctoral Thesis, University of Manitoba, pp. 1-164, 2011.
Hsu et al., "Generation of Se-fortified broccoli as functional food: impact of Se fertilization on S metabolism," Plant, Cell & Environment 34:192-207, 2011.
Joseph et al., "Genetic Variation in the Nuclear and Organellar Genomes Modulates Stochastic Variation in the Metabolome, Growth, and Defense," PLOS Genetics 11(1):e1004779, 2015.
Kliebenstein et al., "Comparative Quantitative Trait Loci Mapping of Aliphatic, Indolic and Benzylic Glucosinolate Production in *Arabidopsis thaliana* Leaves and Seeds," Genetics 159:359-370, 2001.
Lander et al., "MAPMAKER: an interactive computer package for constructing primary genetic linkage maps of experimental and natural populations," *Genomics*; 1(2):174-181, 1987.
Lander et al.,"Mapping mendelian factors underlying quantitative traits using RFLP linkage maps," *Genetics*; 121(1):185-199, 1989.
Lou et al., "Quantitative trait loci for glucosinolate accumulation in *Brassica rapa* leaves," New Phytologist 179(4):1017-1032, 2008.
Mithen et al., "Development of isothiocyanate-enriched broccoli, and its enhanced ability to induce phase 2 detoxification enzymes in mammalian cells." *Theor. and Appl. Genet.*; 106:727-734, 2003.
Office Action issued in Chinese Patent Application No. 2013104297421, dated Dec. 15, 2016.
Office Action issued in New Zealand Patent Application No. 615094, dated Nov. 26, 2014.
Office Action regarding Chinese Patent Application No. 2013104297421, dated Apr. 24, 2019.
Reiter et al., "Global and local genome mapping in *Arabidopsis thaliana* by using recombinant inbred lines and random amplified polymorphic DNAs," *Proc. Natl. Acad. Sci. USA*; 89:1477-1481, 1992.
Rozen et al., "Primer3 on the WWW for general users and for biologist programmers," *Bioinformatics Methods and Protocols: Methods in Molecular Biology*; vol. 132, pp. 365-386, 1999.
Sarikamis et al., "Evaluation of an SSR Marker for Marker-Assisted Selection in Kale (*Brassica oleracea* var. *acephala*)," *Bulgarian Journal of Agricultural Science* 16(1):36-41, 2010.
Sarikamis et al., "High glucosinolate broccoli: a delivery system for sulforaphane," *Molecular Breeding*; 18:219-228, 2006.
Siebert et al., "An improved PCR method for walking in uncloned genomic DNA," *Nucleic Acids Research*; 23(6):1087-1088, 1995.
Super-broccoli a 'fantastic achievement', http://www.smh.com.au/lifestyle/diet-and-fitness/superbrocolli-a-fantastic-achievement-20111005-1l8i2.html, dated Oct. 5, 2011.
'Superbroccoli' goes on sale in UK, http://www.telegraph.co.uk/foodanddrink/8804965/Superbroccoli-goes-on-sale-in UK.html, dated Oct. 4, 2011.
Traka et al., "Genetic regulation of glucoraphanin accumulation in Beneforte broccoli," *New Phytologist* 198(4):1085-1095, 2013.
Wang et al., "Biological Significance of Gene Polymorphism, " *Molecular Trauma*, pp. 389-390; Dec. 31, 2004.
Wentzell et al., "Linking Metabolic QTLs with Network and cis-eQTLs Controlling Biosynthetic Pathways," *PLOS Genetics* 3(9):1687-1701, 2007.
Zang et al., "Genome-wide identification of glucosinolate synthesis genes in *Brassica rapa*," FEBS Journal 276(13):3559-3574, 2009.
Extended European Search Report regarding Europe Application No., dated Feb. 28, 2020.

* cited by examiner

FIG. 1

The B.oleracea lines sequenced to create this consensus are:
GD33
breeder line 560216
breeder ID field number 2153.

The lines that contain the FT69 allele and were used to create this
consensus are:
Breeder line 560526
Breeder line 580333
Breeder line BRM 51-1162
Breeder line BRM51-1210

FT69      1     GAAAATCACAGTTCACGCCTCTTACTCCATGAGCTTCTCTATTCTCATCC
Oleracea  1     GAAAATCACAGTTCACGCCTCTTACTCCATGAGCTTCTCTATTCTCATCC FT69      51    TAGTGTTATAATCTTGCAAACACATATAGAAAGCAAGATTTGGAGTGTAC
Oleracea  51    TAGTGTTATAATCTTGCAAACACATATAGAAAGCAAGGTTTGGAGTGTAC
                                                     -
FT69      101   GAGAAAAACATGAAAACACCTAGAAGCTCTGTGGGTAAGACCCAAGAGCG
Oleracea  101   GAGAAAAACATGAAAACACCTAGAAGCTCTGTGGGTGAGACCCAAGAGCG
                                                   -
FT69      151   TTTCTCGATTAGTTTCATATACAGATGCATCAGAGTTCTCATCAACCGAT
Oleracea  151   TTTCTCGATTAGTTTCATATACAGATGCATCAGAGTTCTCATCAACCGAT FT69      201   CTACTTCTTTCTTATCTTATTAGAAAAAAAAAATCCTATCAAAATTTACT
Oleracea  201   CTACTTCTTTCTTATCTTATTAGAAGAAAAAAATCCTATCAAAATTTACT
                                         -
FT69      251   TTCCTGCAAGTATATTTTTCTTTACATTTTCATTTTCTTGAGTGTTATTT
Oleracea  251   TTCCTGCAAGTATATTTTTCTTTACATTTTCATTTTCTTGAGTGTTATTT FT69      301   GAGTGAAGTTATATTAAAATATT::::::::GTTCATATATATCGAAAAT
Oleracea  301   GAGTGAAGTTATATTAAAATATTGTAATAGAGTTCATATATATCGAAAAT
                                       --------
FT69      351   GTCAAGAAAGCCATGTTGTGTCGGAGAAGGGCTGAAGAAAGGGGCATGGA
Oleracea  351   GTCAAGAAAGCCATGTTGTGTCGGAGAAGGGCTGAAGAAAGGGGCATGGA FT69      401   CCACCGAGGAAGATAAGAAACTCATCTCTTACATCCATGAACATGGAGAA
Oleracea  401   CCACCGAGGAAGATAAGAAACTCATCTCTTACATCCATGAACATGGAGAA FT69      451   GGAGGCTGGCGCGACATTCCTCAAAAAGCTGGTTAATATCTATTATATAT
Oleracea  451   GGAGGCTGGCGCGACATTCCTCAAAAAGCTGGTTAATATCTATTATATAT FT69      501   TTTTTGGTAAATTTTTAAAAC::ATATATGTTTGTTTGGTATTTGATGTA
Oleracea  501   TTTTTGGTAAATTTTTAAAACATATATATGTTTGTTTGGTATTTGATGTA
                                     --
FT69      551   TGAAAGTTTTATATTGAATGTGGTGTTTTACTAGGATTGAAAAGGTGTGG
Oleracea  551   TGAAAGTTTTATGTTGAATATGGTGTTTTACTAGGRTTGAAAAGGTGTGG
                            -
FT69      601   AAAGAGTTGCAGACTGCGATGGACTAACTACCTAAAACCTGAGATCAAAA
Oleracea  601   AAAGAGTTGTAGACTGCGATGGACTAACTACCTAAAACCTGAGATCAAAA
                         -
FT69      651   GAGGCGAGTTTAGTTCAGAGGAGGAACAGATTATCATCATGCTCCATGCT
Oleracea  651   GAGGCGAGTTTAGTTCAGAGGAGGAACAGATTATCATCATGCTCCATGCT

FIG. 1 (continued)

```
FT69       701  GCTCGTGGCAACAAGTACGTTTATTTTAGACCAAAAAAAAACAAGTACGT
Oleracea   701  GCTCGTGGCAACAAGTACGTTTATTTTAGACCAAAAAAAAACAAGTACGT FT69       751  TTATTTTTAACAAAAAGGACGATTATATATTTT::TGTGTGTATGGATCC
Oleracea   751  TTATTTTTAACAAAAAGGACGATTATATATTTTTATGTGTGTATGGATCC FT69       801  TCCAGTGATCATCATTCTAGTTTTCTCTTCTTTTTTTTATACCGCAAACA
Oleracea   801  TCCAGTGATCATCATTCTAGTTTTCTCTTTTTTTTT::ATACCGCAAACA FT69       851  AATTTCATTAGTAAAAAAATTAAAATTCCAAAGTCAATATTCAAAAACA
Oleracea   851  AATTTCATTAGTAAAAAA:TTAAAATTCCAAAGTCAATATTCAAAAACA FT69       901  CAGTGTTATATA::::ATCCTATATATGTCATATATTAAAAAGTATATT
Oleracea   901  CAGTGTTATATATATAATCCTATATATGTCATATATTAAAAAGTA::::

FT69       951  AAAAAAGTACAACATGAGAAATGAATTTAAGTATGCTTCTAAAGCGAAGT
Oleracea   951  ::::::::::CAACATGAGAAATGAATTTAAGTATGCTTCTAAAGCGAAGT FT69      1001  TTTACTTCCCAAAAAATTATTCTTTATTTTTTTCATGTATTTGACAATTC
Oleracea  1001  TTTACTTCCCGAAAAATTATTCTTTATTTTTTTCATGTATTTGACAATTC FT69      1051  TCTGATGCAAAATATGTGTTTGATTAGCAATATGTGACTAAAAATTGCAA
Oleracea  1051  TCTGATGCAAAATATGTGTTTGATTAGCAATATGTGACTAAAAATTGCAA FT69      1101  TAGCACACATCATTTTAGTCTCTATTCCATAGAAAAGCTTCAAAATAAAT
Oleracea  1101  TAGCACACATCATTTTAGTCTCTATTCCATAAAAAAGCTTCAAAATAAAT FT69      1151  TTGATTAACTTTGGTCTTCCATCTTATCTCTTTCACTATTCTTGTCTTTA
Oleracea  1151  TTGATTAACTTTGGTCTTCCATCTTATCTCTTTCACTATTCTTGTCTTTA FT69      1201  GGTGGTCGGTCATAGCKAGACATTTACCTAGAAGAACMGACAATGAGATC
Oleracea  1201  GGTGGTCGGTCATAGCKAGACATTTACCTAGAAGAACMGACAATGAGATC FT69      1251  AAGAAYTACTGGAACACACATCTCAAGAAACGTTTGATCGAACAGGGTAC
Oleracea  1251  AAGAACTACTGGAACACACATCTCAAGAAACGTTTGATCGAACAGGGTAC FT69      1301  TGATCCCGTGACTCACAAGCCACTAGCTTCTAATACAAACCCTACTGTAC
Oleracea  1301  TGATCCCGTGACTCACAAGCCACTAGCTTCTAATACAAACCCTACTGTAC FT69      1351  CTGAGAATTTGCATTCCCTAGATGCATCTAG:::TTCCGACAAGCAATAC
Oleracea  1351  CTGAGAATTTGCATTCCCTAGATGCATCTAGTAATTCCGACAAGCAATAC FT69      1401  TCCCGGTCAAGCTCAATGCCTTCCATGTCTTGTACTCCTTCCTCCGGTTT
Oleracea  1401  TCCCGGTCAAGCTCAATGCCTTCCATGTCTTGTACTCCTTCCTCCGGTTT FT69      1451  CAACACGGTTTTCGAGAATACCAGCAAAGATGGGACACCAGTTCGTGAGG
Oleracea  1451  CAACACGGTTTTCGAGAATACCAGCAAAGATGGGACACCAGTTCGTGAGG FT69      1501  ACGATTCCTTGAGTCGCAAGAAACGTTTGAAGAAATCAAGTTCTACATCA
Oleracea  1501  ACGATTCCTTGAGTCGCAAGAAACGTTTTAAGAAATCAAGTTCTACATCA FT69      1551  AGGCTTTTGAACAAAGTTGCGGCTAAGGCCACTTCCATGAAAAAAGCTTT
Oleracea  1551  AGGCTTTTGAACAAAGTTGCGGCTAAGGCCACTTCCATGAAAGAAGCTTT

FT69      1601  GTCTGCTTCCATGGAAGGTAGCTTGAATGCTAATATAAGCTTTTCCAATG
```

FIG. 1 (continued)

```
Oleracea 1601 GTCTGCTTCCATGGAAGGTAGTTTGAATGCTAATACAAGCTTTTCCAATG

FT69     1651 GCTACTCTGAGCAGATTCTCAATGAAGATGATAGTTCTAATGCATCCCTC
Oleracea 1651 GCTACTCTGAGCAGATTCTCAATGAAGATGATAGTTCTAATGCATCCCTC FT69     1701 ATAAACACTCTCGCCGAGTTCGATCCCTTCCTCCAAACAACGTTTTACCC
Oleracea 1701 ATAAACACTCTCGCCGAGTTCGATCCCTTCCTCCAAACAACGTTTTACCC FT69     1751 TGAGAATGAGATGAATACTACTTCTGATCTCGGTATAGATCAGGACTACT
Oleracea 1751 TGAGAATGAGATGAATACTACTTCTGATCTCGGTATAGATCAGGACTACT FT69     1801 TCTCACATTTTCTCGAAAATTTCGGCA:::::::::ACCATAATGAGGAG
Oleracea 1801 TCTCACATTTTCTCGAAAATTTCGGCAGAGATGATGACCACAATGAGGAG FT69     1851 CACTACATGAATCATAACTATGGTCATGGTCTTCTTATGTCCTATGTGTC
Oleracea 1851 CACTACATGAATCATAACTATGGTCATGATCTTCTTATGTCCGATGTGTC FT69     1901 CCAAGAAGTCTCATCAACTAGCGTTGATGATCAAGACAATACTAATGAGG
Oleracea 1901 CCAAGAAGTCTCATCAACTAGCGTTGATGATCAAGACAATACTAATGAGG FT69     1951 GTTGGTCAAATTATCTTCTTGACCATGCTGATTTATACATGACATGGAT
Oleracea 1951 GTTGGTCAAATTATCTTCTTGACCATGCTGATTTATACATGACATGGAT FT69     2001 TCTGATTCCCTCGGAAAGCATCTCATATGAATCTTCGTGCCTAAGCAGAA
Oleracea 2001 TCTGATTCCCTCGGAAAGCATCTCATATGAATCTTCGTGCCCAAGCAGAA FT69     2051 AGGTTTCAAACT:::::::::TGTCAGAACAAGAAGTTATGTATGTATTC
Oleracea 2051 AGGTTTCAAACTTTTGAAACTTGTCAGAACAAGAAGTTATGTATGTATTC FT69     2101 TATTATATGGATTGTTTAGTATATGTCCAAGATCATGGTTGTTAGTCCCA
Oleracea 2101 TATTATATGGATTGTTTAGTATATGTCCAAGATCATGGTTGTTAGTCCCA FT69     2151 AGTTTAGGGTTTGTATAATATACAATAAGGGACGTTATCTTATAAAACGA
Oleracea 2151 AGTTTAGGGTTTGTATAATATACAATAAGGGACGTTATCTTATAAAACGA FT69     2201 GG
Oleracea 2201 GG
```

FIG. 2a (SEQ ID NO: 1)

*Brassica oleracea Myb28*

```
   1  GAAAATCACAGTTCACGCCTCTTACTCCATGAGCTTCTCTATTCTCATCC
  51  TAGTGTTATAATCTTGCAAACACATATAGAAAGCAAGGTTTGGAGTGTAC
 101  GAGAAAAACATGAAAACACCTAGAAGCTCTGTGGGTGAGACCCAAGAGCG
 151  TTTCTCGATTAGTTTCATATACAGATGCATCAGAGTTCTCATCAACCGAT
 201  CTACTTCTTTCTTATCTTATTAGAAGAAAAAAATCCTATCAAAATTTACT
 251  TTCCTGCAAGTATATTTTCTTTACATTTTCATTTTCTTGAGTGTTATTT
 301  GAGTGAAGTTATATTAAAATATTGTAATAGAGTTCATATATATCGAAAAT
 351  GTCAAGAAAGCCATGTTGTGTCGGAGAAGGGCTGAAGAAGGGGCATGGA
 401  CCACCGAGGAAGATAAGAAACTCATCTCTTACATCCATGAACATGGAGAA
 451  GGAGGCTGGCGCGACATTCCTCAAAAAGCTGGTTAATATCTATTATATAT
 501  TTTTTGGTAAATTTTTAAAACATATATATGTTTGTTTGGTATTTGATGTA
 551  TGAAAGTTTTATGTTGAATATGGTGTTTTACTAGGRTTGAAAAGGTGTGG
 601  AAAGAGTTGTAGACTGCGATGGACTAACTACCTAAAACCTGAGATCAAAA
 651  GAGGCGAGTTTAGTTCAGAGGAGGAACAGATTATCATCATGCTCCATGCT
 701  GCTCGTGGCAACAAGTACGTTTATTTTAGACCAAAAAAAAACAAGTACGT
 751  TTATTTTTAACAAAAAGGACGATTATATATTTTTATGTGTGTATGGATCC
 801  TCCAGTGATCATCATTCTAGTTTTCTCTTTTTTTTTTATACCGCAAACAAA
 851  TTTCATTAGTAAAAAAATTAAAATTCCAAAGTCAATATTCAAAAACACAG
 901  TGTTATATATATAATCCTATATATGTCATATATTAAAAAAGTACAACATG
 951  AGAAATGAATTTAAGTATGCTTCTAAAGCGAAGTTTTACTTCCCGAAAAA
1001  TTATTCTTTATTTTTTTCATGTATTTGACAATTCTCTGATGCAAAATATG
1051  TGTTTGATTAGCAATATGTGACTAAAAATTGCAATAGCACACATCATTTT
1101  AGTCTCTATTCCATAAAAAAGCTTCAAAATAAATTTGATTAACTTTGGTC
1151  TTCCATCTTATCTCTTTCACTATTCTTGTCTTTAGGTGGTCGGTCATAGC
1201  KAGACATTTACCTAGAAGAACMGACAATGAGATCAAGAACTACTGGAACA
1251  CACATCTCAAGAAACGTTTGATCGAACAGGGTACTGATCCCGTGACTCAC
1301  AAGCCACTAGCTTCTAATACAAACCCTACTGTACCTGAGAATTTGCATTC
1351  CCTAGATGCATCTAGTAATTCCGACAAGCAATACTCCGGTCAAGCTCAA
1401  TGCCTTCCATGTCTTGTACTCCTTCCTCCGGTTTCAACACGGTTTTCGAG
1451  AATACCAGCAAAGATGGGACACCAGTTCGTGAGGACGATTCCTTGAGTCG
1501  CAAGAAACGTTTTAAGAAATCAAGTTCTACATCAAGGCTTTTGAACAAAG
```

FIG. 2a (continued)

```
1551 TTGCGGCTAAGGCCACTTCCATGAAAGAAGCTTTGTCTGCTTCCATGGAA
1601 GGTAGTTTGAATGCTAATACAAGCTTTTCCAATGGCTACTCTGAGCAGAT
1651 TCTCAATGAAGATGATAGTTCTAATGCATCCCTCATAAACACTCTCGCCG
1701 AGTTCGATCCCTTCCTCCAAACAACGTTTTACCCTGAGAATGAGATGAAT
1751 ACTACTTCTGATCTCGGTATAGATCAGGACTACTTCTCACATTTTCTCGA
1801 AAATTTCGGCAGAGATGATGACCACAATGAGGAGCACTACATGAATCATA
1851 ACTATGGTCATGATCTTCTTATGTCCGATGTGTCCCAAGAAGTCTCATCA
1901 ACTAGCGTTGATGATCAAGACAATACTAATGAGGGTTGGTCAAATTATCT
1951 TCTTGACCATGCTGATTTTATACATGACATGGATTCTGATTCCCTCGGAA
2001 AGCATCTCATATGAATCTTCGTGCCCAAGCAGAAAGGTTTCAAACTTTTG
2051 AAACTTGTCAGAACAAGAAGTTATGTATGTATTCTATTATATGGATTGTT
2101 TAGTATATGTCCAAGATCATGGTTGTTAGTCCCAAGTTTAGGGTTTGTAT
2151 AATATACAATAAGGGACGTTATCTTATAAAACGAGG
```

FIG. 2b (SEQ ID NO: 2)

*Brassica oleracea Myb28*

```
   1  GAAAATCACAGTTCACGCCTCTTACTCCATGAGCTTCTCTATTCTCATCC
  51  TAGTGTTATAATCTTGCAAACACATATAGAAAGCAAGGTTTGGAGTGTAC
 101  GAGAAAAACATGAAAACACCTAGAAGCTCTGTGGGTGAGACCCAAGAGCG
 151  TTTCTCGATTAGTTTCATATACAGATGCATCAGAGTTCTCATCAACCGAT
 201  CTACTTCTTTCTTATCTTATTAGAAGAAAAAAATCCTATCAAAATTTACT
 251  TTCCTGCAAGTATATTTTTCTTTACATTTTCATTTTCTTGAGTGTTATTT
 301  GAGTGAAGTTATATTAAAATATTGTAATAGAGTTCATATATATCGAAAAT
 351  GTCAAGAAAGCCATGTTGTGTCGGAGAAGGGCTGAAGAAAGGGGCATGGA
 401  CCACCGAGGAAGATAAGAAACTCATCTCTTACATCCATGAACATGGAGAA
 451  GGAGGCTGGCGCGACATTCCTCAAAAAGCTGGTTAATATCTATTATATAT
 501  TTTTTGGTAAATTTTTAAAACATATATATGTTTGTTTGGTATTTGATGTA
 551  TGAAAGTTTTATGTTGAATATGGTGTTTTACTAGGRTTGAAAAGGTGTGG
 601  AAAGAGTTGTAGACTGCGATGGACTAACTACCTAAAACCTGAGATCAAAA
 651  GAGGCGAGTTTAGTTCAGAGGAGGAACAGATTATCATCATGCTCCATGCT
 701  GCTCGTGGCAACAAGTACGTTTATTTTAGACCAAAAAAAAACAAGTACGT
 751  TTATTTTTAACAAAAAGGACGATTATATATTTTTATGTGTGTATGGATCC
 801  TCCAGTGATCATCATTCTAGTTTTCTCTTTTTTTTT<tt>ATACCGCAAACA
 851  AATTTCATTAGTAAAAAAA<a>TTAAAATTCCAAAGTCAATATTCAAAAACA
 901  CAGTGTTATATATATAATCCTATATATGTCATATATTAAAAAAGTA<tatt
 951  aaaaaagta>CAACATGAGAAATGAATTTAAGTATGCTTCTAAAGCGAAGT
1001  TTTACTTCCCGAAAATTATTCTTTATTTTTTTCATGTATTTGACAATTC
1051  TCTGATGCAAATATGTGTTTGATTAGCAATATGTGACTAAAAATTGCAA
1101  TAGCACACATCATTTTAGTCTCTATTCCATAAAAAAGCTTCAAAATAAAT
1151  TTGATTAACTTTGGTCTTCCATCTTATCTCTTTCACTATTCTTGTCTTTA
1201  GGTGGTCGGTCATAGCKAGACATTTACCTAGAAGAACMGACAATGAGATC
1251  AAGAACTACTGGAACACACATCTCAAGAAACGTTTGATCGAACAGGGTAC
1301  TGATCCCGTGACTCACAAGCCACTAGCTTCTAATACAAACCCTACTGTAC
1351  CTGAGAATTTGCATTCCCTAGATGCATCTAGTAATTCCGACAAGCAATAC
1401  TCCCGGTCAAGCTCAATGCCTTCCATGTCTTGTACTCCTTCCTCCGGTTT
1451  CAACACGGTTTTCGAGAATACCAGCAAAGATGGGACACCAGTTCGTGAGG
1501  ACGATTCCTTGAGTCGCAAGAAACGTTTTAAGAAATCAAGTTCTACATCA
1551  AGGCTTTTGAACAAAGTTGCGGCTAAGGCCACTTCCATGAAAGAAGCTTT
1601  GTCTGCTTCCATGGAAGGTAGTTTGAATGCTAATACAAGCTTTTCCAATG
1651  GCTACTCTGAGCAGATTCTCAATGAAGATGATAGTTCTAATGCATCCCTC
1701  ATAAACACTCTCGCCGAGTTCGATCCCTTCCTCCAAACAACGTTTTACCC
1751  TGAGAATGAGATGAATACTACTTCTGATCTCGGTATAGATCAGGACTACT
1801  TCTCACATTTTCTCGAAAATTTCGGCAGAGATGATGACCACAATGAGGAG
1851  CACTACATGAATCATAACTATGGTCATGATCTTCTTATGTCCGATGTGTC
1901  CCAAGAAGTCTCATCAACTAGCGTTGATGATCAAGACAATACTAATGAGG
1951  GTTGGTCAAATTATCTTCTTGACCATGCTGATTTTATACATGACATGGAT
2001  TCTGATTCCCTCGGAAAGCATCTCATATGAATCTTCGTGCCCAAGCAGAA
2051  AGGTTTCAAACTTTTGAAACTTGTCAGAACAAGAAGTTATGTATGTATTC
2101  TATTATATGGATTGTTTAGTATATGTCCAAGATCATGGTTGTTAGTCCCA
2151  AGTTTAGGGTTTGTATAATATACAATAAGGGACGTTATCTTATAAAACGA
2201  GG
```

FIG. 5

(SEQ ID NO: 24 – FT69)

```
   1 GAAAATCACAGTTCACGCCTCTTACTCCATGAGCTTCTCTATTCTCATCC
  51 TAGTGTTATAATCTTGCAAACACATATAGAAAGCAAGATTTGGAGTGTAC
 101 GAGAAAAACATGAAAACACCTAGAAGCTCTGTGGGTAAGACCCAAGAGCG
 151 TTTCTCGATTAGTTTCATATACAGATGCATCAGAGTTCTCATCAACCGAT
 201 CTACTTCTTTCTTATCTTATTAGAAAAAAAAAATCCTATCAAAATTTACT
 251 TTCCTGCAAGTATATTTTTCTTTACATTTTCATTTTCTTGAGTGTTATTT
 301 GAGTGAAGTTATATTAAAATATTGTTCATATATATCGAAAATGTCAAGAA
 351 AGCCATGTTGTGTCGGAGAAGGGCTGAAGAAGGGGCATGGACCACCGAG
 401 GAAGATAAGAAACTCATCTCTTACATCCATGAACATGGAGAAGGAGGCTG
 451 GCGCGACATTCCTCAAAAAGCTGGTTAATATCTATTATATATTTTTGGT
 501 AAATTTTTAAAACATATATGTTTGTTTGGTATTTGATGTATGAAAGTTTT
 551 ATATTGAATGTGGTGTTTTACTAGGATTGAAAAGGTGTGGAAAGAGTTGC
 601 AGACTGCGATGGACTAACTACCTAAAACCTGAGATCAAAAGAGGCGAGTT
 651 TAGTTCAGAGGAGGAACAGATTATCATCATGCTCCATGCTGCTCGTGGCA
 701 ACAAGTACGTTTATTTTAGACCAAAAAAAAACAAGTACGTTTATTTTTAA
 751 CAAAAAGGACGATTATATATTTTTGTGTGTATGGATCCTCCAGTGATCAT
 801 CATTCTAGTTTTCTCTTCTTTTTTTTATACCGCAAACAAATTTCATTAGT
 851 AAAAAAAATTAAAATTCCAAAGTCAATATTCAAAAACACAGTGTTATATA
 901 ATCCTATATATGTCATATATTAAAAAAGTATATTAAAAAAGTACAACATG
 951 AGAAATGAATTTAAGTATGCTTCTAAAGCGAAGTTTTACTTCCCAAAAAA
1001 TTATTCTTTATTTTTTTCATGTATTTGACAATTCTCTGATGCAAAATATG
1051 TGTTTGATTAGCAATATGTGACTAAAAATTGCAATAGCACACATCATTTT
1101 AGTCTCTATTCCATAGAAAAGCTTCAAAATAAATTTGATTAACTTTGGTC
1151 TTCCATCTTATCTCTTTCACTATTCTTGTCTTTAGGTGGTCGGTCATAGC
1201 KAGACATTTACCTAGAAGAACMGACAATGAGATCAAGAAYTACTGGAACA
1251 CACATCTCAAGAAACGTTTGATCGAACAGGGTACTGATCCCGTGACTCAC
1301 AAGCCACTAGCTTCTAATACAAACCCTACTGTACCTGAGAATTTGCATTC
1351 CCTAGATGCATCTAGTTCCGACAAGCAATACTCCCGGTCAAGCTCAATGC
1401 CTTCCATGTCTTGTACTCCTTCCTCCGGTTTCAACACGGTTTTCGAGAAT
1451 ACCAGCAAAGATGGGACACCAGTTCGTGAGGACGATTCCTTGAGTCGCAA
1501 GAAACGTTTGAAGAAATCAAGTTCTACATCAAGGCTTTTGAACAAAGTTG
1551 CGGCTAAGGCCACTTCCATGAAAAAAGCTTTGTCTGCTTCCATGGAAGGT
1601 AGCTTGAATGCTAATATAAGCTTTTCCAATGGCTACTCTGAGCAGATTCT
1651 CAATGAAGATGATAGTTCTAATGCATCCCTCATAAACACTCTCGCCGAGT
1701 TCGATCCCTTCCTCCAAACAACGTTTTACCCTGAGAATGAGATGAATACT
1751 ACTTCTGATCTCGGTATAGATCAGGACTACTTCTCACATTTTCTCGAAAA
1801 TTTCGGCAACCATAATGAGGAGCACTACATGAATCATAACTATGGTCATG
1851 GTCTTCTTATGTCCTATGTGTCCCAAGAAGTCTCATCAACTAGCGTTGAT
1901 GATCAAGACAATACTAATGAGGGTTGGTCAAATTATCTTCTTGACCATGC
1951 TGATTTTATACATGACATGGATTCTGATTCCCTCGGAAAGCATCTCATAT
2001 GAATCTTCGTGCCTAAGCAGAAAGGTTTCAAACTTGTCAGAACAAGAAGT
2051 TATGTATGTATTCTATTATATGGATTGTTTAGTATATGTCCAAGATCATG
2101 GTTGTTAGTCCCAAGTTTAGGGTTTGTATAATATACAATAAGGGACGTTA
2151 TCTTATAAAACGAGG
```

GENETIC MARKERS FOR MYB28

CROSS REFERENCE TO RELATED APPLICATIONS

This application is a divisional of U.S. application Ser. No. 15/359,471, filed Nov. 22, 2016, which is a divisional of U.S. application Ser. No. 14/025,737, filed Sep. 12, 2013, now U.S. Pat. No. 9,567,650, which claims benefit of U.S. Provisional Application No. 61/700,731, filed Sep. 13, 2012, each herein incorporated by reference in their entirety.

INCORPORATION OF SEQUENCE LISTING

The sequence listing that is contained in the file named "SEMB009US_ST25.txt", which is 21 kilobytes as measured in Microsoft Windows operating system and was created on Aug. 28, 2013, is filed electronically herewith and incorporated herein by reference.

FIELD OF THE INVENTION

The present invention relates to the identification of molecular markers tightly linked with the transcription factor Myb28 locus conferring increased glucosinolate levels, and methods for producing Cruciferous vegetable plants with increased glucosinolate levels.

BACKGROUND OF THE INVENTION

Cruciferous vegetable plants (such as *Brassica* plants like broccoli) accumulate 4-methylsulphinylbutyl glucosinolate (glucoraphanin) and 3-methylsulphinylbutyl glucosinolate (glucoiberin). These glucosinolates are hydrolysed to isothiocyanates. Epidemiological studies correlate diets rich in cruciferous vegetables with a reduction in a risk of cancer. High glucosinolate Cruciferous vegetables (e.g. high glucosinolate broccoli) have been developed as described in WO99/52345 and PCT/GB2009/001648. The production of glucosinolates in Cruciferous vegetable plants is complex as can be seen from the map of sulphur flux in plants shown in FIG. 4. Prior to the present invention methylthioalkylmalate synthase (MAM) metabolic or molecular markers were used in breeding programs. It was known that MAM1 and MAM3 closely associated with high glucosinolate traits.

The present inventors surprisingly observed that some *Brassica* cultivars with high glucosinolate (e.g. glucoraphanin) phenotype did not possess the MAM marker alleles though to be associated with the trait, thus concluding that the MAM markers were not necessarily closely linked to or the key to the high glucosinolate profile and therefore their use as markers in breeding was not reliable for the tracking of this trait.

The inventors therefore sought a marker for high glucosinolates which could be reliably and consistently used to determine the genotype of a plant with an increased glucosinolate level.

SUMMARY OF THE INVENTION

A seminal finding of the present invention is that the transcription factor Myb28 locus is a key locus in the production of increased levels of glucosinolates, particularly 4-methylsulphinylbutyl glucosinolate (glucoraphanin) and 3-methylsulphinylbutyl glucosinolate (glucoiberin) in Cruciferous vegetable plants (such as *Brassica* plants, for instance, broccoli).

For the first time the present inventors have shown that polymorphisms can be observed in the transcription factor Myb28 locus between high glucosinolate Cruciferous vegetable plants (e.g. *Brassica villosa*) and Cruciferous vegetable plants that do not show the high glucosinolate phenotype (e.g. *Brassica oleracea*) and that these polymorphisms can be used as molecular markers for determining the genotype of a Cruciferous vegetable plant (such as a *Brassica* plant, for instance broccoli) for modified (e.g. increased) glucosinolate levels and/or in marker assisted breeding for plants with modified (e.g. increased) glucosinolate levels.

In a first aspect of the present invention there is provided a method for determining the genotype of a Cruciferous vegetable plant with an increased glucosinolate level, comprising obtaining a sample of nucleic acids from said plant or a portion thereof and detecting in said nucleic acids a polymorphism at the Myb28 locus that is genetically linked to an increased glucosinolate level.

A further aspect of the present invention provides a method of producing a Cruciferous vegetable plant having Myb28-mediated increased glucosinolate levels, which method comprises selecting first progeny plants comprising a polymorphism at the Myb28 locus that is genetically linked to increased glucosinolate levels.

In a yet further aspect, the present invention provides a plant or a part thereof (e.g. an inflorescence) produced by a method of the present invention.

The present invention further provides a seed of a plant of the present invention or a seed of a plant produced by a method of the present invention.

In a further aspect, the present invention provides an isolated nucleic acid comprising a sequence selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEC) ID NO: 20, SEQ ID NO; 21, SEQ ID NO: 22 and SEQ ID NO: 23.

In another aspect, the present invention provides a primer or probe that amplifies and/or hybridizes to at least one polymorphism at a position corresponding to nucleotide 83, 136, 226, 563, 610, 830, 995, 1116, 1513, 1577, 1606, 1620, 1825, 1863, 1877 or 2026 of SEQ ID NO:1; or that amplifies and/or hybridizes to a polymorphism present between positions corresponding to nucleotides 323 and 332, between nucleotides 521 and 524, between nucleotides 783 and 786, between nucleotides and 909 and 914, between nucleotides 1365 and 1369, between 1811 and 1821, or between nucleotides 2046 and 2056 of SEQ ID NO: 1; or that amplifies and/or hybridizes to a polymorphism present between nucleotides 836 and 837, between nucleotides 867 and 868, or between nucleotides 943 and 944 of SEQ ID NO: 1.

In certain embodiments, the step of detecting or selecting comprises PCR and/or DNA hybridization.

In some embodiments, determining the genotype comprises a co-dominant assay.

In one embodiment, the screening method comprises detecting a co-dominant genetic marker.

In one embodiment the polymorphism comprises at least one of:
  a. a single nucleotide polymorphism (SNP) at a position corresponding to nucleotide 83, 136, 226, 563, 610, 830, 995, 1116, 1513, 1577, 1606, 1620, 1825, 1863, 1877 or 2026 of SEQ ID NO: 1, or b. a polymorphism in the number of nucleotides present between nucleotides 323 and 332, between nucleotides 521 and 524, between nucleotides 783 and 786, between nucleotides and 909 and 914, between nucleotides 1365 and 1369, between 1811 and 1821, or between nucleotides 2046 and 2056 of SEQ ID NO: 1, or c. a polymorphism in the number of nucleotides present between nucleotides 836 and 837, between nucleotides 867 and 868, or between nucleotides 943 and 944 of SEQ ID NO: 1.

In one embodiment the polymorphism comprises at least one of a single nucleotide polymorphism (SNP) at a position corresponding to nucleotide 83, 136, 226, 563, 610, 830, 995, 1116, 1513, 1577, 1606, 1620, 1825, 1863, 1877 or 2026 of SEQ ID NO: 1 or combinations thereof.

In another embodiment the polymorphism comprises a deletion of one or more of the nucleotides present between nucleotides 323 and 332, between nucleotides 521 and 524, between nucleotides 783 and 786, between nucleotides 909 and 914, between nucleotides 1365 and 1369, between 1811 and 1821, or between nucleotides 2046 and 2056 of SEQ ID NO: 1.

In another embodiment the polymorphism comprises a deletion of two or more of the nucleotides present between nucleotides 323 and 332, between nucleotides 909 and 914, between nucleotides 1365 and 1369, between 1811 and 1821, or between nucleotides 2046 and 2056 of SEQ ID NO: 1.

In another embodiment the polymorphism comprises a deletion of three or more of the nucleotides present between nucleotides 323 and 332, between nucleotides 909 and 914, between 1811 and 1821, or between nucleotides 2046 and 2056 of SEQ ID NO: 1.

In another embodiment the polymorphism comprises a deletion of four or more (e.g. 5 or more, or 6 or more, or 7 or more) of the nucleotides present between nucleotides 323 and 332, between 1811 and 1821, or between nucleotides 2046 and 2056 of SEQ ID NO: 1.

In another embodiment the polymorphism comprises a deletion of eight or more of the nucleotides present between 1811 and 1821, or between nucleotides 2046 and 2056 of SEQ ID NO: 1.

In another embodiment the polymorphism comprises a deletion of all of the nucleotides present between nucleotides 323 and 332, or all of the nucleotides between nucleotides 521 and 524, or all of the nucleotides between nucleotides 783 and 786, or all of the nucleotides between nucleotides 909 and 914, or all of the nucleotides between nucleotides 1365 and 1369, or all of the nucleotides between 1811 and 1821, or all of the nucleotides between nucleotides 2046 and 2056 of SEQ ID NO: 1.

In another embodiment the polymorphism comprises a deletion of at least one of the nucleotides present between nucleotides 323 and 332, or at least one of the nucleotides between nucleotides 521 and 524, or at least one of the nucleotides between nucleotides 783 and 786, or at least one of the nucleotides between nucleotides 909 and 914, or at least one of the nucleotides between nucleotides 1365 and 1369, or at least one of the nucleotides between 1811 and 1821, or at least one of the nucleotides between nucleotides 2046 and 2056 of SEQ ID NO: 1, or combinations thereof.

In further embodiment the polymorphism comprises a deletion of at least one nucleotide at a position corresponding to nucleotide 324, 325, 326, 327, 328, 329, 330, 331, 522, 523, 784, 785, 910, 911, 912, 913, 1366, 1367, 1368, 1812, 1813, 1814, 1815, 1816, 1817, 1818, 1819, 1820, 2047, 2048, 2049, 2050, 2051, 2052, 2053, 2054, or 2055 of SEQ ID NO: 1.

In one embodiment, the polymorphism comprises a deletion of the nucleotides at the following positions: 324-331, 522-523, 784-785, 910-913, 1366-1368, 1812-1820 or 2047-2055 of SEQ ID NO: 1 or combinations thereof.

In one embodiment, the polymorphism comprises an insertion of one or more nucleotides between the nucleotides 836 and 837, 867 and 868, or 943 and 944 of SEQ ID NO: 1.

When the polymorphism is an insertion of one or more nucleotides between the nucleotides 836 and 837, then suitably the insertion is of two nucleotides. When two nucleotides are inserted between the nucleotides 836 and 837 then suitably the nucleotides may be TT.

When the polymorphism is an insertion of one or more nucleotides between the nucleotides 867 and 868, then suitably the insertion is of one nucleotide. When one nucleotide is inserted between the nucleotides 867 and 868 then suitably the nucleotide may be A.

When the polymorphism is an insertion of one or more nucleotides between the nucleotides 943 and 944, then suitably the insertion is of up to and including 13 nucleotides. When 13 nucleotides are inserted between the nucleotides 943 and 944 then suitably the nucleotides may be TATTAAAAAAGTA (SEQ ID NO:25).

In some embodiments the polymorphism is more than one (suitably more than 2, suitably more than 3, suitably more than 4, suitably more than 5, suitably all) of the following polymorphisms:

a. a single nucleotide polymorphism (SNP) at a position corresponding to nucleotide 83, 136, 226, 563, 610, 830, 995, 1116, 1513, 1577, 1606, 1620, 1825, 1863, 1877 or 2026 of SEQ ID NO: 1, or b. a polymorphism in the number of nucleotides present between nucleotides 323 and 332, between nucleotides 521 and 524, between nucleotides 783 and 786, between nucleotides and 909 and 914, between nucleotides 1365 and 1369, between 1811 and 1821, or between nucleotides 2046 and 2056 of SEQ ID NO: 1, or c. a polymorphism in the number of nucleotides present between nucleotides 836 and 837, between nucleotides 867 and 868, or between nucleotides 943 and 944 of SEQ ID NO: 1.

In particular embodiments, the polymorphism is detected by a screening method comprising use of at least a first sequence selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22 and SEQ ID NO: 23.

In one embodiment, the method of producing a Cruciferous vegetable plant comprises the steps of: (a) crossing a Cruciferous vegetable plant having an increased glucosinolate level with a second Cruciferous vegetable; and (b) selecting at least a first progeny Cruciferous vegetable plant comprising a polymorphism at the Myb28 locus that is genetically linked to increasing glucosinolate levels.

In one embodiment selecting the first progeny comprises selecting the progeny based on the presence of one or more genetic markers from the second Cruciferous vegetable plant genetically linked to at least a first additional trait. In a further embodiment of the method, the additional trait may be selected from the group consisting of: yield, disease resistance, emergence vigour, vegetative vigour, stress tolerance, plant height, inflorescence quality, inflorescence diameter, inflorescence weight, inflorescence size, inflorescence shape, inflorescence colour, and number of days to flowering.

In one embodiment a method of producing a Cruciferous vegetable having Myb28-mediated increased glucosinolate levels, may further comprise the step of (c) crossing the progeny plant with itself or a third plant to produce a progeny plant of a subsequent generation and may further comprise the steps of: (d) crossing the progeny plant of a subsequent generation with itself or a second plant; and (e) repeating steps (c) and (d) for an additional 3-10 generations to produce an inbred Cruciferous vegetable plant comprising an increased level of glucosinolate, wherein the progeny plant of at least one subsequent generation is screened for the presence of a polymorphism at the Myb28 locus genetically linked to glucosinolate production. In one embodiment, the progeny plant of a subsequent generation is selected for crossing based on the presence of glucosinolates and a desired trait. In the method, step (e) is repeated with sufficient inbreeding to obtain an inbred Cruciferous vegetable plant that comprises an increased glucosinolate trait and otherwise comprises the agronomic traits of the second broccoli plant.

In particular embodiments the methods of the present invention may further comprise assaying the phenotype of a broccoli plant for an increased level of a glucosinolate.

In one preferable embodiment of the present invention the glucosinolate is 4-methylsulphinylbutyl glucosinolate (MSB).

In one preferable embodiment the Cruciferous vegetable plant (e.g. *Brassica* plant, such as broccoli) comprises at least one glucosinolate in amount of at least 10 micromol/g dry weight.

In one embodiment the Cruciferous vegetable plant comprises 4-methylsulphinylbutyl glucosinolate (MSB), 3-methylsulphinylpropyl glucosinolate (MSP) or combinations thereof in an amount of at least 10 micromol/g dry weight.

In one embodiment the Cruciferous vegetable plant comprises 4-methylsulphinylbutyl glucosinolate (MSB) in an amount of at least 10 micromol/g dry weight.

In one embodiment, the term "Cruciferous vegetable plant with an increased glucosinolate level" means a Cruciferous vegetable plant comprising 4-methylsulphinylbutyl glucosinolate (MSB), 3-methylsulphinylpropyl glucosinolate (MSP) or combinations thereof in an amount of at least 10 micromol/g dry weight.

In one embodiment, the term "Cruciferous vegetable plant with an increased glucosinolate level" means a Cruciferous vegetable plant comprising 4-methylsulphinylbutyl glucosinolate (MSB) in an amount of at least 10 micromol/g dry weight.

In one embodiment the Cruciferous vegetable plant according to the present invention is a *Brassica* plant.

In one embodiment the Cruciferous vegetable plant according to the present invention is broccoli.

In still yet another aspect, the invention provides a method comprising recording on a computer readable medium the genotype of a plant or population of plants for at least a first polymorphism detected in accordance with the invention. The invention also provides a computer readable medium containing such information.

In a yet further aspect, the present invention provides a method of producing an edible portion of the Cruciferous vegetable plants (e.g. *Brassica* plants, such as broccoli) comprising: (a) obtaining a plant by a method of the present invention; and (b) collecting the edible portions (e.g. inflorescences) produced by the plant.

In a further aspect of the present invention there is provided an isolated nucleic acid comprising a sequence of at least 18 contiguous nucleotides that are conserved between SEQ ID NO: 1 and SEQ ID NO: 24 when aligned.

The present invention yet further provides, an isolated nucleic acid comprising a sequence of at least 18 contiguous nucleotides of SEQ ID NO: 1, wherein the sequence is not present within SEQ ID NO: 24.

In a yet further aspect the present invention provides an isolated nucleic acid comprising a sequence of at least 18 contiguous nucleotides of SEQ ID NO: 24, wherein the sequence is not present within SEQ ID NO: 1.

For the avoidance of doubt all numbering of nucleotide positions as used herein correspond with the nucleotide numbering given in SEQ ID NO: 1 or by alignment with SEQ ID NO:1.

BRIEF DESCRIPTION OF THE DRAWINGS

FIG. 1 shows a sequence alignment between a consensus sequence of the Myb28 locus for broccoli, e.g. *B. villosa*, with an increased level of glucosinolate (FT69) and a consensus sequence of the Myb28 locus for broccoli, e.g. *B. oleracea*, which does not have an increased level of glucosinolate (*oleracea*). A total of 26 single feature polymorphisms (SFPs) (of which there are 16 SNPs and 10 indels) are detected in a sequence with a total length of 2202 bp. The SFPs are shaded in the sequence alignment shown in FIG. 1. These SFPs are indicative of *B. villosa* introgression.

FIG. 2a shows SEQ ID NO: 1; a sequence of a nucleic acid fragment comprising the Myb28 locus from *Brassica oleracea* (broccoli) which does not have increased glucosinolate levels. The SFPs (including SNPs and indels, e.g. nucleotides that can be deleted) are shaded. The nucleotides between which an SFP (indel insertion) may be inserted are underlined.

FIG. 2b shows SEQ ID NO: 2; a sequence of a nucleic acid fragment comprising the Myb28 locus from *Brassica oleracea* (broccoli) which does not have increased glucosinolate levels. The SFPs (including SNPs and indels, e.g. nucleotides that can be deleted) are shaded. Fragments in brackets < > (and lower case nucleotides) correspond to SFPs (indels, that are insertions) in the *Brassica oleracea* sequence which insertions are found in high glucosinolate broccoli (e.g. *Brassica villosa*).

FIG. 5 shows SEQ ID NO: 24; a sequence of a nucleic acid fragment comprising the Myb28 locus from *Brassica villosa* FT69 (broccoli) which has increased glucosinolate levels. The shaded nucleotides indicate SFPs (including SNPs and indels) when aligned with SEQ ID NO: 1.

DETAILED DISCLOSURE OF THE PREFERRED EMBODIMENTS OF THE INVENTION

Figure 3:
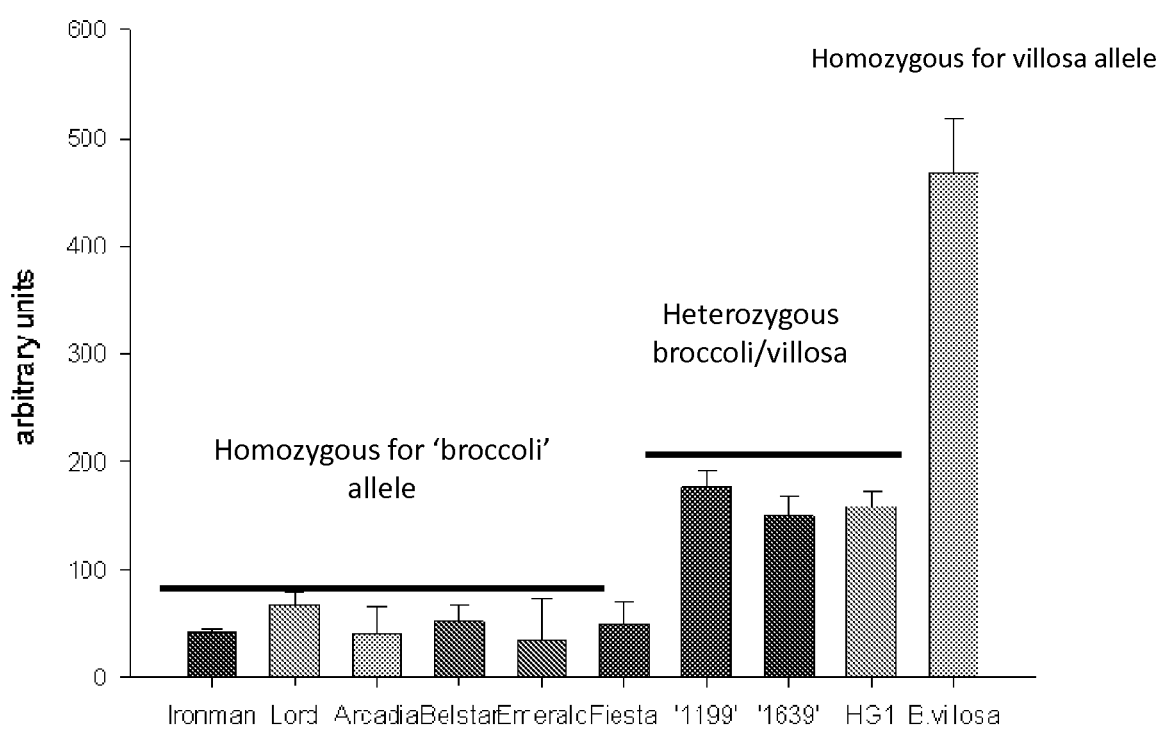
FIG. 3 shows Myb28 expression in leaves of broccoli cultivars (the 1199, 1639 and HG1 cultivars all being high glucosinolate—e.g. high glucoraphanin—cultivars).

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure.

Numeric ranges are inclusive of the numbers defining the range. Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure.

The headings provided herein are not limitations of the various aspects or embodiments of this disclosure which can be had by reference to the specification as a whole. Accordingly, the terms defined immediately below are more fully defined by reference to the specification as a whole.

Other definitions of terms may appear throughout the specification. Before the exemplary embodiments are described in more detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that such publications constitute prior art to the claims appended hereto.

The present invention relates to identification of an amplifiable and assayable polymorphic locus Myb28, a transcription factor gene closely linked to conference of increased glucosinolate levels to plants. This polymorphic locus may be termed the "Myb28-FT69" or "FT69" locus or "*Brassica villosa*" locus. One or more genetic marker(s) at this locus, such as DNA polymorphism(s), e.g., one or more single nucleotide polymorphism(s) (SNP) or an insertion/deletion ("indel") can thus be used as genetic marker(s) to detect the presence of the high glucosinolate trait locus.

The polymorphic locus may be defined as comprising an allele that is genetically linked to and identifies a phenotype of increased levels of glucosinolate, or an allele that is genetically linked to and identifies a phenotype of an absence of increased levels of glucosinolate.

Thus, the invention provides specific molecular haplotypes at the Myb28 locus that are associated with the presence or absence of increased glucosinolate level gene allele.

In one embodiment, a Myb28-FT69 (increased glucosinolate) sequence is represented as the FT69 sequence shown in FIG. 1.

In another embodiment, a Myb28-FT69 (increased glucosinolate) sequence is represented as the FT69 sequence shown as SEQ ID NO: 24 (in FIG. 5).

Line FT-69 is a line developed by the John Innes Center, UK which has elevated levels of 3-methylthiopropyl glucosinolate (MSP) (glucoiberin). It was created by crossing a wild relative of domesticated broccoli, *Brassica villosa*, with a domesticated broccoli, *Brassica oleracea*. FT-69 was backcrossed to the adapted broccoli plant line BRM 51-19. After each cross, plants were selected based on phenotype similarities to the recurrent parent BRM 51-19, and analysed for levels of MSP and the additional phytochemical 4-methylsulphinylbutyl glucosinolate (MSB) (glucoraphanin). The finished line was named BRM 51-1162.

The inventors determined that broccoli (*Brassica oleracea*) contributes the genes to produce the target glucosinolate, e.g. 4-methylsulphinylbutyl glucosinolate (MSB) (glucoraphanin), and *B. villosa* contributes the genes to increase the concentration of the target glucosinolate.

The present invention thus allows use of polymorphic sites at the Myb28 locus to efficiently select for plants with increased glucosinolate levels even under high selection pressure for other traits such as yield, disease resistance, emergence vigor, vegetative vigor, stress tolerance, plant height, inflorescence quality, inflorescence diameter, inflorescence weight, inflorescence size, inflorescence shape, inflorescence colour, and number of days to flowering, among others.

The present invention also provides FOR primers and reaction conditions whereby a marker, such as a SNP or indel specific to plants comprising increased levels of glucosinolates, can be detected in a dominant or co-dominant manner. Through use of the markers, one of skill in the art may select for an increased level of a glucosinolate during breeding of a Cruciferous vegetable plant (e.g. *Brassica* plant, such as broccoli).

Previously described markers linked to the high glucosinolate trait fail to provide an adequate selection tool because, for instance, the previously described markers are not tightly linked to increased glucosinolate levels.

In another aspect, the present invention provides a method of introgressing increased glucosinolate levels into a Cruciferous vegetable plant (e.g. *Brassica* plant, such as broccoli) comprising: (a) crossing a Cruciferous vegetable plant having an increased glucosinolate level with a second Cruciferous vegetable to form a segregating population; and (b) selecting at least one member of the population exhibiting an increased glucosinolate trait, wherein selection is based on the presence of a detectable haplotype at the Myb28-FTS9 locus. In one aspect, the pepper line having the increased glucosinolate trait is crossed with the second Cruciferous vegetable plant (e.g. *Brassica* plant, such as broccoli) line for at least two generations (e.g., creating either an F2 or BC1S1 population). In another aspect, plants are identified as having increased glucosinolate phenotype prior to crossing. In one aspect, the segregating population is self-crossed and the subsequent population is screened for increased glucosinolate levels.

As used herein, a "marker" is an indicator for the presence of at least one phenotype, genotype, or polymorphism. Markers include, but are not limited to, single nucleotide polymorphisms (SNPs), cleavable amplified polymorphic sequences (CAPS), amplified fragment length polymorphisms (AFLPs), restriction fragment length polymorphisms (RFLPs), simple sequence repeats (SSRs), insertion(s)/deletion(s) (INDEL(s)), inter-simple sequence repeats (ISSR), sequence characterized amplified region (SCAR) markers, and random amplified polymorphic DNA (RAPD) sequences.

A marker may be inherited in co-dominant fashion (both alleles at a locus in a diploid heterozygote are readily detectable), with no environmental variance component, i.e., heritability of 1.

A "nucleic acid marker" as used herein means a nucleic acid molecule that is capable of being a marker for detecting a polymorphism, phenotype, or both associated with an increased glucosinolate level.

Use of a marker at the Myb28 locus provides rapid and reliable molecular screening of candidate lines, and allows for genotypic screening of Cruciferous vegetable (e.g. Brassica plant, such as broccoli) breeding lines for an increased glucosinolate level without the necessity of a phenotypic phytochemical assay.

Once plants having increased glucosinolate levels are produced, the plants themselves can be cultivated in accordance with conventional procedures. Progeny may be obtained through sexual reproduction. The seeds resulting from sexual reproduction can be recovered from plants having increased glucosinolate levels and planted or otherwise grown as a means of propagation. Progeny may also be obtained from plants through asexual reproduction. Protoplast or propagules (e.g., cuttings, scions or rootstocks) can be recovered from plants with an increased glucosinolate level or parts thereof and may be employed to propagate plants with an increased glucosinolate level.

The present invention also provides progeny of plants having an increased glucosinolate level, produced by the presently described methods. As used herein, progeny include not only, without limitation, the products of any cross (be it a backcross or otherwise) between two plants, but all progeny whose pedigree traces back to the original cross. In one aspect of the present invention, the progeny contain about 50%, 25%, 12.5% or less nuclear DNA from a plant having an increased glucosinolate level and expresses the genetic material that provides an increased glucosinolate level.

As used herein, linkage of two nucleic acid sequences, including a nucleic acid marker sequence and a nucleic acid sequence of a genetic locus imparting a desired trait such as increased glucosinolate levels, may be genetic or physical or both.

In one aspect of the invention, the nucleic acid marker and genetic locus conferring an increased glucosinolate trait are genetically linked, for instance exhibiting a LOD score of greater than 2.0, as judged by interval mapping for the increased glucosinolate trait based on maximum likelihood methods described by Lander and Botstein, 1989 (*Genetics* 121: 185-199), and implemented in the software package MAPMAKER (e.g., Lander et al., (1987) *Genomics* 1: 174-181; default parameters). In other embodiments, the marker and region conferring an increased glucosinolate trait are genetically linked and exhibit a LOD score of greater than 3.0, or a LOD score of greater than 6.0, 9.0, 12.0, 15.0, or 18.0.

In another aspect, the nucleic acid molecule may be physically linked to Myb28 locus. In some aspects, the nucleic acid marker specifically hybridizes to a nucleic acid molecule having a sequence that is within the Myb28 locus.

As used herein, two nucleic acid molecules are said to be capable of hybridizing to one another if the two molecules are capable of forming an anti-parallel, double-stranded nucleic acid structure. Conventional stringency conditions are described by Sambrook et al. (1989) (Molecular Cloning, A Laboratory Manual, $2^{nd}$ Ed., Cold Spring Harbor Press, Cold Spring Harbor, N.Y.), and by Haymes et al. (1985) (Nucleic Acid Hybridization, A Practical Approach, IRL Press, Washington, D.C.). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization, for example, 6.0*sodium chloride/sodium citrate (SSC) at about 45 deg. C., followed by a wash of 2.0*SSC at 50 deg. C., are known to those skilled in the art or can be found in Ausubel et al. (1989) (Current Protocols in Molecular Biology, John Wiley & Sons, N.Y.), Section 6.3.1-6.3.6. In some embodiments, hybridization conditions can be high, moderate or low stringency conditions. Exemplary conditions include those using 50% formamide, 5.0*SSC, 1% SDS and incubation at 42 deg. C. for 14 hours, followed by a wash using 0.2*SSC, 1% SDS and incubation at 65 deg. C.

The specificity of hybridization can be affected by post-hybridization washes. For example, the salt concentration in the wash step can be selected from a low stringency of about 2.0*SSC at 50 deg. C. to a moderate stringency of about 1.0*SSC at 50 deg. C. to a high stringency of about 0.2*SSC at 50 deg. C. In addition, the temperature in the wash step can be increased from low stringency conditions at room temperature, about 22 deg. C., to moderate stringency conditions at about 50 deg. C., to high stringency conditions at about 65 deg. C. Both temperature and salt concentration may be varied, or either the temperature or the salt concentration may be held constant while the other variable is changed. In some aspects, the wash step can be performed for 5, 10, 15, 20, 25, 30, or more minutes. In another aspect, the wash step is performed for about 20 minutes. In yet another aspect, the wash step can be repeated 1, 2, 3, 4, or more times using the selected salt concentration, temperature, and time. In another aspect, the wash step is repeated twice.

A genetic marker profile of a plant may be predictive of the agronomic traits of a hybrid produced using that inbred. For example, if an inbred plant of known genetic marker profile and phenotype is crossed with a second inbred of known genetic marker profile and phenotype it is possible to predict the phenotype of the F1 hybrid based on the combined genetic marker profiles of the parent inbreds. Methods for prediction of hybrid performance from genetic marker data are disclosed in U.S. Pat. No. 5,492,547, the disclosure of which is specifically incorporated herein by reference in its entirety. Such predictions may be made using any suitable genetic marker, for example, SSRs, INDELs, RFLPs, AFLPs, SNPs, ISSRs, or isozymes.

Additional markers, such as SSRs, AFLP markers, RFLP markers, RAPD markers, phenotypic markers, SNPs, SCAR markers, isozyme markers, or microarray transcription profiles that are genetically linked to or correlated with Myb28-mediated increased glucosinolate levels can be utilized. Methods to isolate such markers are known in the art.

For example, locus-specific SSRs can be obtained by screening a genomic library for markers specific to sequences found on the genomic clone of Myb28-FT69, sequencing of "positive" clones, designing primers which flank the repeats, and amplifying genomic DNA with these primers.

As used herein, the progeny include not only, without limitation, the products of any cross (be it a backcross or otherwise) between two plants, but all progeny whose pedigree traces back to the original cross. Specifically, without limitation, such progeny include plants that have 50%, 25%, 12.5% or less nuclear DNA derived from one of the two originally crossed plants.

As used herein, a second plant is derived from a first plant if the second plant's pedigree includes the first plant.

The present invention provides a genetic complement of the Cruciferous vegetable (e.g. Brassica, such as broccoli) lines described herein. Further provided is a hybrid genetic complement, wherein the complement is formed by the combination of a haploid genetic complement from elite inbred Cruciferous vegetable (e.g. Brassica such as broccoli) lines described herein and another haploid genetic complement. Means for determining such a genetic complement are well-known in the art.

As used herein, the phrase "genetic complement" means an aggregate of nucleotide sequences, the expression of which defines the phenotype of a plant, such as a broccoli plant or a cell or tissue of that plant. By way of example, a broccoli plant is genotyped to determine a representative sample of the inherited markers it possesses. Markers may be inherited in co-dominant fashion so that the presence of both alleles at a diploid locus are readily detectable, and they are free of environmental variation, i.e., their heritability is close to, or equal to, 1. This genotyping is preferably performed on at least one generation of the descendant plant for which the numerical value of the trait or traits of interest are also determined. The array of single locus genotypes is expressed as a profile of marker alleles, two at each locus for a diploid plant. The marker allelic composition of each locus can be either homozygous or heterozygous. Homozygosity is a condition where both alleles at a locus are characterized by the same conditions of the genome at a locus (e.g., the same nucleotide sequence). Heterozygosity refers to different conditions of the genome at a locus. Potentially any type of genetic marker could be used, for example, simple sequence repeats (SSRs), insertion/deletion polymorphism (INDEL), restriction fragment length polymorphisms (RFLPs), amplified fragment length polymorphisms (AFLPs), single nucleotide polymorphisms (SNPs), and isozymes.

Considerable genetic information can be obtained from a completely classified F2 population using a co-dominant marker system (e.g., Mather, 1938 Measurements of Linkage in Heredity: Meuthuen & Co). An F2 population is the first generation of self or sib pollination after the hybrid seed is produced. Usually a single F1 plant is self or sib pollinated to generate a population segregating for the nuclear-encoded genes in a Mendelian (1:2:1) fashion.

In contrast to the use of co-dominant markers, using dominant markers often requires progeny tests (e.g., F3 or back cross self families) to identify heterozygous individuals. The information gathered can be equivalent to that obtained in a completely classified F2 population. Marker-assisted selection can then be applied to subsequent progeny based on marker-trait map associations (F2, F3), where linkage has not been completely disassociated by recombination events (i.e., maximum disequilibrium).

Recombinant inbred lines (RILs) (genetically related lines; usually >F5) can be used as a mapping population. RILs can be developed by selfing F2 plants, then selfing the resultant F3 plants, and repeating this generational selling process, thereby increasing homozygosity. Information obtained from dominant markers can be maximized by using RILs because all loci are homozygous or nearly so. Under conditions of tight linkage (i.e., about <10% recombination), dominant and co-dominant markers evaluated in RIL populations provide more information per individual than either marker type in backcross populations (e.g., Reiter et al., 1992 (*Proc. Natl. Acad. Sci.* (*USA*) 89: 1477-1481). However, as the distance between markers becomes larger (i.e., loci become more independent), the information in RIL populations decreases dramatically when compared to co-dominant markers.

Backcross populations can be utilized as mapping populations. A backcross population (BC) can be created by crossing an F1 to one of its parents. Typically, backcross populations are created to recover the desirable traits (which may include most of the genes) from a recurrent parental line (the parent that is employed in the backcrosses) while adding one or a few traits from the second parental line, which is often referred to as the donor. A series of backcrosses to the recurrent parent can be made to recover most of the recurrent parent's desirable traits. Thus a population is created consisting of individuals nearly like the recurrent parent, wherein each individual carries varying amounts or a mosaic of genomic regions from the donor parent. Backcross populations can be useful for mapping dominant markers particularly if all loci in the recurrent parent are homozygous and the donor and recurrent parent have contrasting polymorphic marker alleles (Reiter el al., 1992).

Information obtained from backcross populations using either co-dominant or dominant markers is less than that obtained from completely classified F2 populations because recombination events involving one, rather than two, gametes are sampled per plant. Backcross populations, however, are more informative (at low marker saturation) when compared to RILs as the distance between linked loci increases in RIL populations (i.e., about 15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the loci are polymorphic between the parental lines and would be expected to segregate in the highly homozygous NIL population. Those loci that are polymorphic in a NIL population, however, are likely to be linked to the trait of interest.

Plants generated using a method of the present invention can be part of or generated from a breeding program. The choice of breeding method depends on the mode of plant reproduction, the heritability of the trait(s) being improved, and the type of cultivar used commercially (e.g., F1 hybrid cultivar, pure line cultivar, etc). Selected, non-limiting approaches for breeding the plants of the present invention are set forth below. A breeding program can be enhanced using marker assisted selection of the progeny of any cross. It is further understood that any commercial and non-commercial cultivars can be utilized in a breeding program. Factors such as, for example, yield, disease resistance, emergence, vigor, vegetative vigor, stress tolerance, plant height, inflorescence quality, inflorescence diameter, inflorescence weight, inflorescence size, inflorescence shape, inflorescence colour, and number of days to flowering will generally dictate the choice.

For highly heritable traits, a choice of superior individual plants evaluated at a single location will be effective, whereas for traits with low heritability, selection should be based on statistical analyses (e.g., mean values) obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favourable genes for a highly heritable trait into a desirable cultivar. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates as parents for new commercial cultivars; those still deficient in traits may be used as parents for hybrids, or to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated self or sib pollinating and selection, producing many new genetic combinations.

The development of new Cruciferous vegetable (e.g. *Brassica*, such as broccoli) lines requires the development and selection of Cruciferous vegetable (e.g. *Brassica*, such as broccoli) varieties, the crossing of these varieties and selection of superior hybrid crosses. The hybrid seed can be produced by manual crosses between selected male-fertile parents or by using male sterility systems. Hybrids can be selected for certain single gene traits. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes into parent lines. These lines are used to produce new cultivars. New cultivars can be evaluated to determine which have commercial potential.

Pedigree breeding is used commonly for the improvement of self-pollinating crops. Two parents who possess favourable, complementary traits are crossed to produce an F1. An F2 population is produced by selfing one or several F1's. Selection of the best individuals in the best families is performed. Replicated testing of families can begin in the F4 generation to improve the effectiveness of selection for traits with low heritability. At an advanced stage of inbreeding (i.e., F6 and F7), the best lines or mixtures of phenotypically similar lines are tested for potential release as new cultivars.

Backcross breeding and cross breeding have been used to transfer genes for a simply inherited, highly heritable trait into a desirable homozygous cultivar or inbred line, which is the recurrent parent. The source of the trait to be transferred is called the donor parent. The resulting plant obtained from a successful backcrossing program is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. After multiple backcrossing generations with selection, the resulting line is expected to have the attributes of the recurrent parent (e.g., cultivar) and the desirable trait transferred from the donor parent.

Plants generated by the invention may be generated using a single-seed descent procedure. The single-seed descent procedure, in the strict sense, refers to planting a segregating population, then selecting one plant in this and each subsequent generation to self and create the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

Descriptions of other breeding methods that are commonly used for different traits and crops can be found in one of several reference books available (e.g., Fehr, 1987, Principles of Cultivar Development Vol. 1, pp. 2-3).

In another aspect, Cruciferous vegetable (e.g. *Brassica*, such as broccoli) lines having increased glucosinolate levels can be used in breeding programs to combine increased glucosinolate levels with additional traits of interest.

As used herein, reference to a Cruciferous vegetable having an increased level of glucosinolate (such as a broccoli having an increased level of glucosinolate) and/or at least one derivative thereof, refers to broccoli having an increased level of at least one phytochemical selected from a list comprising: 4-methylsulphinylbutyl glucosinolate, 3-methylsulphinylpropyl glucosinolate, 4-methylthiobutyl glucosinolate; 3-methylthiopropyl glucosinolate, sulforaphane, erucin, sativin, iberin, β-phenylethylisothiocyanate (PE-ITC), 3-methylthiopropyl isothiocyanate.

Cruciferous vegetables (e.g. broccoli) having a high level of glucosinolate are described in WO99/52345 and PCT/GB2009/001648, both of which are incorporated herein by reference.

Suitably the Cruciferous vegetable with increased glucosinolate levels (such as *Brassica* or broccoli with increased glucosinolate levels) may comprise increased levels of one or more glucosinolate and/or one or more isothiocyanate.

In one embodiment the Cruciferous vegetable with increased glucosinolate levels (such as *Brassica* or broccoli with increased glucosinolate levels) for use in the present invention comprises increased levels of one or more of the following compounds: 4-methylsulphinylbutyl glucosinolate (MSB), 3-methylsulphinylpropyl glucosinolate (MSP), 4-methylthiobutyl glucosinolate; 3-methylthiopropyl glucosinolate.

In one embodiment the Cruciferous vegetable with increased glucosinolate levels (such as *Brassica* or broccoli with increased glucosinolate levels) for use in the present invention comprises increased levels 4-methylsulphinylbutyl glucosinolate (MSB) and/or 3-methylsulphinylpropyl glucosinolate (MSP).

Preferably the Cruciferous vegetable with increased glucosinolate levels (such as *Brassica* or broccoli with increased glucosinolate levels) has a level of 4-methylsulphinylbutyl glucosinolate (MSB) which is 2 to 3 times the level of 4-methylsulphinylbutyl glucosinolate (MSB) found in a standard Cruciferous vegetable (such as a standard *Brassica* or standard broccoli) grown under similar conditions.

Suitably the Cruciferous vegetable with increased glucosinolate levels (such as *Brassica* or broccoli with increased glucosinolate levels) may have a level of 4-3-methylsulphinylpropyl glucosinolate (MSP) which is 2 to 3 times the level of 4-3-methylsulphinylpropyl glucosinolate (MSP) found in a standard Cruciferous vegetable (such as a standard *Brassica* or standard broccoli) grown under similar conditions.

Suitably the Cruciferous vegetable with increased glucosinolate levels (such as *Brassica* or broccoli with increased glucosinolate levels) may comprise at least one glucosinolate in an amount of at least 10 micromol/g dry weight. More preferably at least about 14µ moles/g dry weight, at least about 16µ moles/g dry weight, at least about 20µ moles/g dry weight, at least about 25µ moles/g dry weight, at least about 30µ moles/g dry weight, at least about 50µ moles/g dry weight or at least about 75µ moles/g dry weight.

Suitably, in one embodiment the Cruciferous vegetable with increased glucosinolate levels (such as *Brassica* or broccoli with increased glucosinolate levels) may have either 4-methylsulphinylbutyl glucosinolate (MSB) and/or 3-methylsulphinylpropyl glucosinolate (MSP) in an amount of at least 10 micromol/g dry weight. More preferably at least about 14µ moles/g dry weight, at least about 16µ moles/g dry weight, at least about 20µ moles/g dry weight, at least about 25µ moles/g dry weight, at least about 30µ moles/g dry weight, at least about 50µ moles/g dry weight or at least about 75µ moles/g dry weight.

Glucosinolates are a class of organic compounds that contain sulphur, nitrogen and a group derived from glucose. They occur as secondary metabolites of many plants of the order Brassicales (especially in the family Brassicaceae), such as Cruciferous vegetables.

Glucosinolates are water-soluble anions and belong to the glucosides. Every glucosinolate contains a central carbon atom which is bonded via a sulphur atom to the glycone group (making a sulfated ketoxime) and via a nitrogen atom to a sulphate group. In addition, the central carbon is bonded to a side group; different glucosinolates have different side groups.

About 120 different glucosinolates are known to occur naturally in plants.

The glucosinolates in accordance with the present invention are preferably aliphatic.

In the present invention it is envisaged that one or more of the following glucosinolates may be of importance: 4-methylsulphinylbutyl glucosinolate, 3-methylsulphinylpropyl glucosinolate, 4-methylthiobutyl glucosinolate and 3-methylthiopropyl glucosinolate.

In one embodiment the glucosinolate is preferably 4-methylsulphinylbutyl glucosinolate (MSB) and/or 3-methylsulphinylpropyl glucosinolate (MSP).

In one embodiment the glucosinolate is preferably 4-methylsulphinylbutyl glucosinolate (MSB).

Many useful traits can be introduced by genetic transformation techniques. Genetic transformation may therefore be used to insert a selected transgene into a *Brassica* plant of the invention or may, alternatively, be used for the preparation of transgenes, which can be introduced by backcrossing. Methods for the transformation of plants, including *Brassica*, are well known to those of skill in the art.

Vectors used for the transformation of plant cells are not limited so long as the vector can express an inserted DNA in the cells. For example, vectors comprising promoters for constitutive gene expression in *Brassica* cells (e.g., cauliflower mosaic virus 35S promoter) and promoters inducible by exogenous stimuli can be used. Examples of suitable vectors include pBI binary vector. The "*Brassica* cell" into which the vector is to be introduced includes various forms of *Brassica* cells, such as cultured cell suspensions, protoplasts, leaf sections, and callus.

A vector can be introduced into *Brassica* cells by known methods, such as the polyethylene glycol method, polycation method, electroporation, *Agrobacterium*-mediated transfer, particle bombardment and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

One efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded can be positioned at an appropriate distance below the macroprojectile stopping plate. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium* (and other *Rhizobia*), allowing for convenient manipulations. Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (U.S. Pat. No. 5,563,055). For example, U.S. Pat. No. 5,349,124 describes a method of transforming plant cells using *Agrobacterium*-mediated transformation. By inserting a chimeric gene having a DNA coding sequence encoding for the full-length B.t. toxin protein that expresses a protein toxic toward Lepidopteran larvae, this methodology resulted in plants having resistance to such insects.

A number of promoters have utility for plant gene expression for any gene of interest including but not limited to selectable markers, scorable markers, genes for pest tolerance, disease resistance, nutritional enhancements and any other gene of agronomic interest. Examples of constitutive promoters useful for *Brassica* plant gene expression include, but are not limited to, the cauliflower mosaic virus (CaMV) P-35S promoter, which confers constitutive, high-level expression in most plant tissues, including monocots; a tandemly duplicated version of the CaMV 35S promoter, the enhanced 35S promoter (P-e35S) the nopaline synthase promoter, the octopine synthase promoter; and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

Exemplary nucleic acids which may be introduced to the plants of this invention include, for example, DNA sequences or genes from another species, or even genes or sequences which originate within or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a *Brassica* plant according to the invention.

In one embodiment the myb28 gene having one or more of the polymorphisms taught herein may be introduced into a *Brassica* plant by transforming a *Brassica* plant with said gene.

In one embodiment the present invention relates to transforming a *Brassica* plant with a myb28 gene comprising SEQ ID NO: 1 except for at least one polymorphism selected from the group consisting of:

a) a single nucleotide polymorphism (SNP) at a position corresponding to nucleotide 83, 136, 226, 563, 610, 830, 995, 1116, 1513, 1577, 1606, 1620, 1825, 1863, 1877 or 2026 of SEQ ID NO: 1, or b) a polymorphism in the number of nucleotides present between nucleotides 323 and 332, between nucleotides 521 and 524, between nucleotides 783 and 786, between nucleotides and 909 and 914, between nucleotides 1365 and 1369, between 1811 and 1821, or between nucleotides 2046 and 2056 of SEQ ID NO: 1, or c) a polymorphism in the number of nucleotides present between nucleotides 836 and 837, between nucleotides 867 and 868, or between nucleotides 943 and 944 of SEQ ID NO: 1.

In one embodiment the present invention relates to transforming a *Brassica* plant with a myb28 gene comprising SEQ ID NO: 24 or a sequence which has a least 97% (such as at least 98% or at least 99%) identity with SEQ ID NO: 24.

In some embodiments further genes and corresponding phenotypes may be introduced into a *Brassica* plant including by way of example one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, DNA coding sequences can affect phenotypes by encoding a non-translatable RNA molecule that causes the targeted inhibition of expression of an endogenous gene, for example via antisense- or co-suppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest may be used in the present invention.

An Increased Level of Glucosinolate

Suitably the terms "Cruciferous vegetable plant with an increased glucosinolate level" or "broccoli with an increased glucosinolate level"" means a Cruciferous vegetable or broccoli plant, respectively, with an increased level of glucosinolates compared with a traditional variety of that Cruciferous vegetable or of broccoli. In broccoli the traditional variety may be *B. oleraceae* GD33, breeder line 560216 or breeder ID field number 2153.

The term "an increased glucosinolate level" in one embodiment means that the Cruciferous vegetable (such as broccoli) has a level of 4-methylsulphinylbutyl glucosinolate (MSB) and/or methylsulphinylpropyl glucosinolate (MSP) which is 2 to 3 times the level of 4-methylsulphinylbutyl glucosinolate (MSB) and/or methylsulphinylpropyl glucosinolate (MSP) found in a standard (traditional variety of) Cruciferous vegetable (such as a standard [traditional variety of] broccoli) grown under similar conditions.

Suitably the term "an increased glucosinolate level" in one embodiment means that the Cruciferous vegetable (such as broccoli) comprises between about 10 and about 100µ moles/g dry weight. Suitably the term "an increased glucosinolate level" means that the Cruciferous vegetable (such as broccoli) comprises at least about 10µ moles/g dry weight, suitably at least about 14µ moles/g dry weight, suitably at least about 16µ moles/g dry weight, suitably at least about 20µ moles/g dry weight, suitably at least about 25µ moles/g dry weight, suitably at least about 30µ moles/g dry weight, suitably at least about 50µ moles/g dry weight, suitably at least about 75µ moles/g dry weight. Cruciferous vegetables (such as broccoli) with an increased glucosinolate level are described in Mithen et al *Theor. Appl. Genet.* (2003) 106, 727-734; Sarikamis et al *Molecular Breeding* (2006) 18, 219-228, or in WO 99/52345 (incorporated herein by reference).

In one embodiment the Cruciferous vegetable (such as broccoli) with an increased glucosinolate level may comprise 4-methylsulfinylbutyl glucosinolate and/or 3-methylsulfinylpropyl glucosinolate at concentrations of between about 10 and about 100µ moles/g dry weight, suitably of about 14 and about 100µ moles/g dry weight, suitably of about 16 and about 100µ moles/g dry weight, suitably of between about 20 and about 100µ moles/g dry weight, suitably of between about 30 and about 100µ moles/g dry weight, suitably of between about 50 and about 100µ moles/g dry weight.

For example, the level of 4-methylsulfinylbutyl glucosinolate in a Cruciferous vegetable (such as broccoli) with an increased glucosinolate level for instance may be between about 8 to about 55µ moles/g dry weight, suitably between about 10 to about 55µ moles/g dry weight, suitably between about 10 to about 40µ moles/g dry weight. Suitably, the level of 4-methylsulfinylbutyl glucosinolate in a Cruciferous vegetable (such as broccoli) with an increased glucosinolate level for instance may be at least about 8µ moles/g dry weight, suitably at least about 10µ moles/g dry weight, suitably at least about 15µ moles/g dry weight. This contrasts sharply with Cruciferous vegetables (in particular broccoli) available from retail outlets which typically has levels of this glucosinolate in the region of 4-5µ moles/g dry weight.

For example, the level of 3-methylsulfinylpropyl glucosinolate in a Cruciferous vegetable (such as broccoli) with an increased glucosinolate level for instance may be between about 1.5 to about 10µ moles/g dry weight, suitably between about 2 to about 10µ moles/g dry weight, suitably between about 2 to about 8µ moles/g dry weight. Suitably, the level of 3-methylsulfinylpropyl glucosinolate in a Cruciferous vegetable (such as broccoli) with an increased glucosinolate level for instance may be at least about 1.5µ moles/g dry weight, suitably at least about 2µ moles/g dry weight, suitably at least about 3µ moles/g dry weight, suitably at least about 4µ moles/g dry weight, suitably at least about 5µ moles/g dry weight. This contrasts sharply with Cruciferous vegetables (such as broccoli) available from retail outlets which typically has levels of this glucosinolate in the region of 0.5-1µ moles/g dry weight.

In one embodiment the levels of glucosinolates in the Cruciferous vegetable (such as the broccoli) is determined by examining all edible parts of the plant, such as both the inflorescences and edible stems for broccoli. In another embodiment the level of glucosinolates in the Cruciferous vegetable (such as broccoli) is determined by examining the leaves only or the inflorescences only or the roots only.

For instance where the Cruciferous vegetable is one where the leaves are mainly eaten—such as rocket, salad rocket, wall rocket, wild rocket, kale or cabbage for instance, then preferably the level of glucosinolates in the Cruciferous vegetable is determined by examining the leaves only.

Where the Cruciferous vegetable is one where the inflorescences are mainly eaten—such as broccoli, Brussel sprouts or cauliflower for instance, then preferably the level of glucosinolates in the Cruciferous vegetable is determined by examining the inflorescences only.

Where the Cruciferous vegetable is one where the roots are mainly eaten—such as radish or turnip for instance, then preferably the level of glucosinolates in the Cruciferous vegetable is determined by examining the edible part of the root only.

Preferably it is at least the broccoli inflorescences (or only the broccoli inflorescences) which are used in the present invention.

In one embodiment the term "an increased glucosinolate level" means that the Cruciferous vegetable inflorescences or edible roots or edible leaves contain the increased glucosinolate level, for example of between about 10 and about 100µ moles/g dry weight. In this embodiment suitably the term "an increased glucosinolate level" means that the Cruciferous vegetable inflorescences or roots or leaves comprise at least about 10µ moles/g dry weight, suitably at least about 14µ moles/g dry weight, at least about 16µ moles/g dry weight, suitably at least about 20µ moles/g dry weight, suitably at least about 25µ moles/g dry weight, suitably at least about 30µ moles/g dry weight, suitably at least about 50µ moles/g dry weight, suitably at least about 75µ moles/g dry weight.

In one embodiment the term "an increased glucosinolate level" means that the broccoli inflorescences contain the high level of glucosinolate, for example of between about 10 and about 100µ moles/g dry weight. In this embodiment suitably the term "an increased glucosinolate level" means that the broccoli inflorescences comprise at least about 10µ moles/g dry weight, suitably at least about 14µ moles/g dry weight, at least about 16µ moles/g dry weight, suitably at least about 20µ moles/g dry weight, suitably at least about 25µ moles/g dry weight, suitably at least about 30µ moles/g dry weight, suitably at least about 50µ moles/g dry weight, suitably at least about 75µ moles/g dry weight. It will be understood that the term Cruciferous vegetable having an increased glucosinolate level (such as broccoli having an increased glucosinolate level) refers not only to the plant material in its fresh natural state i.e. as whole heads, such as broccoli inflorescences and stems, but also to the Cruciferous vegetable (such as the broccoli) when it has been subjected to one or more further processing steps such as, for example floreting, individual quick freezing (IQF), maceration, homogenization, drying, freezing, compacting, etc.

Cruciferous Vegetables

The skilled person will be aware that plants comprising glucosinolate other than high glucosinolate broccoli are known. Glucosinolate is present in plants from the order Capparales. This order includes about 18 families, of which the Brassicaceae and the Capparaceae are the two largest.

Cruciferous vegetables (e.g. cruciferous vegetable crops) from the family Brassicaceae containing glucosinolate include the following cruciferous vegetable crops:

broccoli rocket (including *Sisymbrium officinales*; *Eruca sativa* (Salad Rocket), *Diplotaxis erucoides* (Wall Rocket), *Diplotaxis tenuifolia* (Wild Rocket), and *Bunias orientalis* (Turkish Rocket)); and watercress (including *Rorripa nasturtium aquaticum* and *Nasturtium officinale*).

cauliflower, kale, turnip, collards,
kohlrabi,
Brussels sprouts,
Chinese cabbage,
canola,
cabbage, and
radish.

Those of skill in the art will appreciate the many advantages of the methods and compositions provided by the present invention. The following examples are included to demonstrate the preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention. All references cited herein are incorporated herein by reference to the extent that they supplement, explain, provide a background for, or teach methodology, techniques, or compositions employed herein.

EXAMPLES

Figure 4:
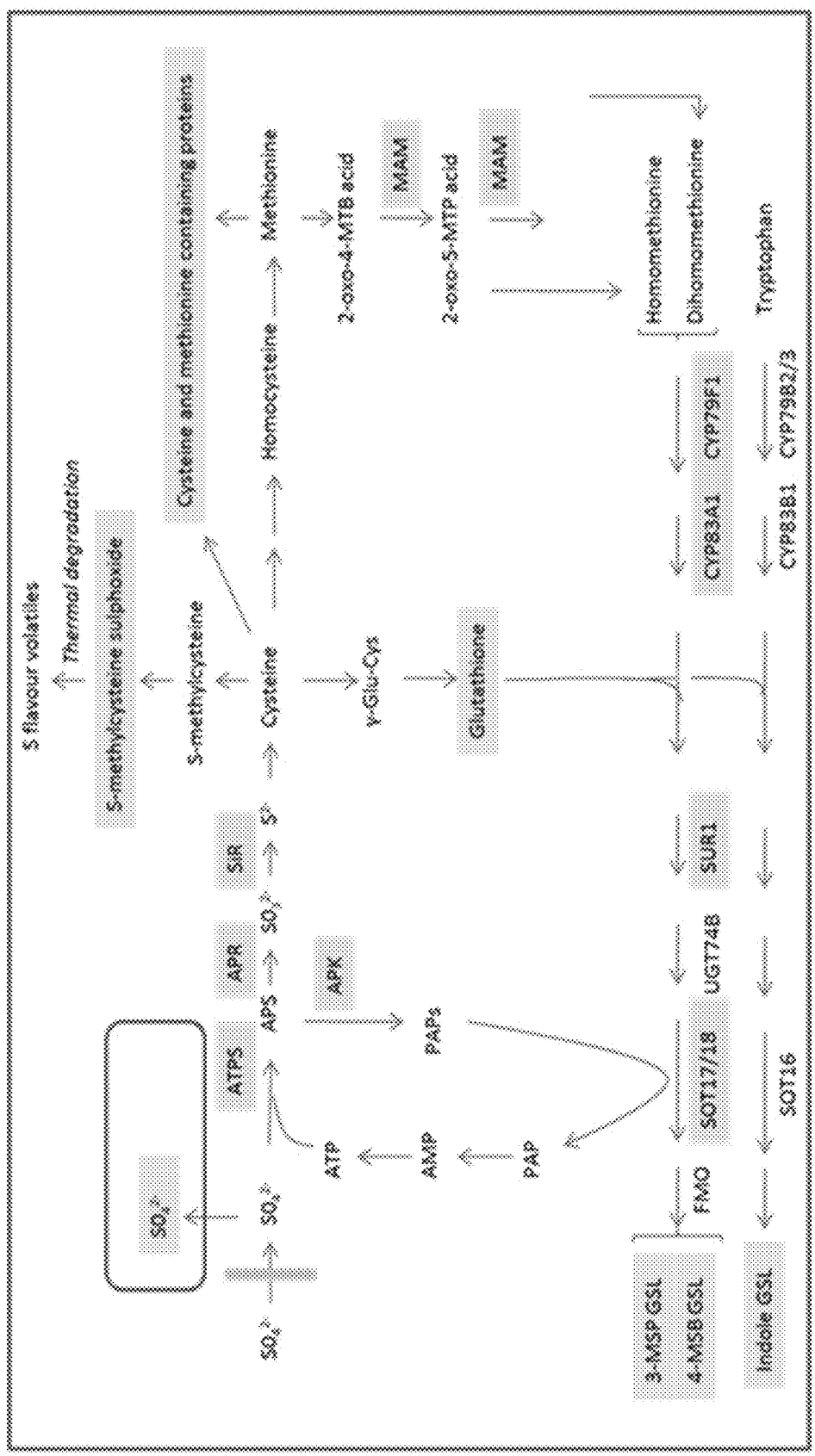
FIG. 4 shows a schematic of the sulphur flux in *Brassica* plants. Metabolites in yellow are the main S pools.

The production of glucosinolates in Cruciferous vegetables is complex. FIG. 4 shows a schematic of sulphur flux in *Brassica*. Cruciferous vegetables with an increased level of glucosinolates (e.g. broccoli with an increased level of glucosinolates) have been developed, e.g. as described in WO99/52345 and PCT/GB2009/001648 (incorporated herein by reference).

*Brassica villosa* has a very high level of 3-methylthiopropyl glucosinolates. When crossed with broccoli (*Brassica oleracea*), this is converted into 4-methylsulphinylbutyl glucosinolate (glucoraphanin). The inventors have determined that *B. villosa* contributes the genes to increase the amount of glucosinolate produced in a *Brassica* plant.

It is found that the high glucoraphanin trait is dominant, so it is only necessary to be introgressed into one inbred/double haploid parent for hybrids. A double haploid broccoli breeding line derived from the cultivar Green Duke (referred to as GD DH, Bouhuon, E. J. R., Keith, D. J., Parkin, I. A. P., Sharpe, A. G., & Lydiate, D. J. (1996) *Theor. Appl. Genet.* 93, 833-839) is available.

Prior to the present invention methylthioalkylmalate synthase (MAM) metabolic or molecular markers were used in breeding programs. It was known that MAM1 and MAM3 closely associated with high glucosinolate traits.

However, the present inventors surprisingly observed that some *Brassica* cultivars with high glucosinolate (e.g. glucoraphanin) phenotype did not possess the MAM marker alleles thought to be associated with the trait, thus concluding that the MAM markers were not necessarily closely linked to or the key to the high glucosinolate profile and therefore their use as markers in breeding was not reliable for the tracking of this trait.

The inventors therefore sought a marker for high glucosinolates which could be reliably and consistently used to determine the genotype of a plant with an increased glucosinolate (particularly an increased glucoraphanin) level.

The inventors have surprisingly identified the transcription factor Myb28 locus as a key locus that regulates methionine-derived glucosinolate biosynthesis in Cruciferous vegetables (e.g. broccoli).

Example 1

Real-Time RT-PCR of MYB28

Myb28 sequence was identified by BLAST® search using the *B. rapa* sequence for Myb28 (Bra029311) at the BRAD *Brassica* database (Cheng et al., 2011 BRAD, *the genetics and genomics database for Brassica plants. BMC Plant Biology* 2011; 11:136. doi: 10.1186/1471-2229-11-136). The assay was designed using ABI PRISM Primer Express Software v2 (Applied Biosystems). Primers and TaqMan probe with 5'-FAM and 3'-TAMRA modifications were purchased from MWG UK and sequences (SEQ ID NOs: 26-28) are:

```
Myb28 For
5'-CTCTTCCTCTTTCCTCGGGTTT-3',

Myb28 Rev
5'-TGCAACTCAAGGAACCTCTCTGA-3',

Myb28 probe
5'-AACCCGGTTTCCGAGATCACCACAC-3'.
```

Myb28 mRNA levels were determined by real time RT-PCR using the ABI Prism Step One Plus Sequence Detection System (Applied Biosystems). The real time RT-PCR reactions were carried out in a microamp optical 96-well plate in a total volume of 20 µl per well containing Taqman® RNA-TO-CT 1-Step master mix reagent kit (Applied Biosystems), 20 ng total RNA, 0.25 Uul$^{-1}$ Multiscribe™ and optimised concentrations of primers and probes.

Real time RT-PCR conditions were as follows: one cycle of 48° C. for 30 min, one cycle of 95° C. for 10 min followed by 40 cycles at 95° C. for 15 sec and one cycle at 60° C. for 1 min.

Myb28 data were analysed using a standard curve generated by a serial dilution of total RNA from one Ironman plant.

FIG. 3 shows Myb28 expression in leaves of broccoli cultivars (the 1199, 1639 and HG1 cultivars all being cultivars with increased glucosinolate levels—e.g. increased glucoraphanin cultivars.

MYB28 Sequencing

The Myb28 sequence is identified by BLAST® search using the *B. rapa* sequence for Myb28 (Bra029311) at the BRAD *Brassica* database (Cheng, F.; Liu, S.; Wu, J.; Fang, L.; Sun, S.; Liu, B.; Li, P.; Hua, W.; Wang, X., BRAD, The genetics and genomics database for *Brassica* plants. *BMC Plant Biology* 2011, 11, 136).

Primers are designed using Primer3 version 0.4.0 (Rozen S, S. H. J., Primer3 on the WWW for general users and for biologist programmers. In *Bioinformatics Methods and Protocols: Methods in Molecular Biology*, Krawetz S, M. S., Ed. Humana Press: Totowa, N.J., 2000; pp 365-386) and purchased from MWG UK.

DNA is extracted from leaf material using the QIAGEN DNeasy Plant Maxi kit (QIAGEN).

```
MYB28 For
                                      (SEQ ID NO: 3)
5'-TCACGAACATGGAGAAGGTG-3',
```

MYB28 REV (SEQ ID NO: 4)

TGAGCTTGACCGGGAGTATC-3'.

PCR reactions are performed in a total volume of 20 µl containing 1× Green GoTaq® Reaction Buffer (Promega), 2.5 mM MgCl$_2$, 0.2 mM dNTPs, 0.2 µM primers, 0.5 units GoTaq® DNA Polymerase and 15-50 ng DNA.

PCR conditions are as follows: 95° C. for 2 min followed by 35 cycles of 95° C. for 30 sec, 53° C. for 1 min and 72° C. for 1 min, before the final extension at 72° C. for 5 min. PCR products are run by gel electrophoresis on an agarose gel and purified using the QIAquick Gel Extraction Kit (QIAGEN) before sending to TGAC (Norwich, UK) for sequencing.

Example 2

Identification of Polymorphisms in the Myb28 Coding Region Between *B. villosa* and *B. oleracea* Breeding Lines Using MYB28 mRNA complete coding sequence from *Brassica oleracea* var italic R2R3 (NCBI accession number GQ478992.1), primers were designed by hand (Table 1) to amplify fragments between 300 and 500 bp.

TABLE 1 sequences of primers (SEQ ID NOs: 3-23) designed upon *B. oleracea* coding sequence to amplify Myb28 fragments in different breeding lines for sequencing. These primers were designed by hand.

| Primer name | Sequence (5' > 3') | Size | Comment |
|---|---|---|---|
| OD00876 | TCACGAACATGGAGAAGGTG | 20 | |
| OD00877 | TGAGCTTGACCGGGAGTATC | 20 | combi with 876 |
| OD00878 | CTAACTACCTAAAACCTGAG | 20 | |
| OD00879 | CTAGTGGCTTGTGAGTCAC | 19 | combi with 878 |
| OD00880 | CCTCGTTTTATAAGATAACGTC | 22 | coding sequence |
| OD00881 | CTCGATATAGATCAGGACTAC | 21 | combi with 880 |
| OD00882 | GATGAGACTTCTTGGGACAC | 20 | coding sequence |
| OD00883 | GAGGACGATTCCTTGAGTC | 19 | combi with 882 |
| OD00884 | ACCTTCCATGGAAGCAGAC | 19 | coding sequence |
| OD00885 | TGTGTTTGATTAGCAATATGTG | 22 | combi with 884 |
| OD00886 | AGCAGCATGGAGCATGATG | 19 | coding sequence |
| OD00887 | TGTGTCGGAGAAGGGCTG | 18 | combi with 886 |
| OD00888 | CCAGCCACCTTCTCCATG | 18 | coding sequence |
| OD00889 | ACGCCTCTTACTCCATGAG | 19 | combi with 888 |
| OD00890 | TCCTATCAAAATTTACTTTCCTG | 23 | coding sequence |
| OD00891 | CAGTCTGCAACTCTTTCCAC | 20 | combi with 890 |
| OD00892 | CTTTAGGTGGTCGGTCATAG | 20 | coding sequence |
| OD00893 | TCAGGGTAAAACGTTGTTTG | 20 | combi with 892 |
| OD00951 | TGTATTTGACAATTCTCTGATG | 22 | replacement 892 combi with 884 |
| OD00952 | TTCATGGAAGTGGCCTTAG | 19 | nested of 884 |
| OD00953 | CTTGGGACTAACAACCATGA | 20 | nested of 880 combi with 881 |

The primers in Table 1 are designated SEQ ID NO: 3 to SEQ ID NO: 23, respectively, herein. Using these primers, fragments were amplified from individuals containing the FT69 allele from *B. villosa* and individuals containing the *B. oleracea* allele. The individuals used to identify the *B. oleracea* allele were randomly chosen from breeding material. Different segments of the coding sequence were amplified from individuals containing the FT69 *B. villosa* allele and the *B. oleracea* allele, DNA was extracted from leaf material using Whatman filter plates. PCR reactions were performed in a total volume of 20 µl containing 1×PCR buffer containing MgCl$_2$, 0.2 mM dNTPs, 0.1 µM primers, 0.4 units DreamTaq® DNA Polymerase (Fermentas) and 50-100 ng DNA.

PCR conditions as follow: 95° C. for 2 min followed by 35 cycles of 95° C. for 30 sec, 56° C. for 30 sec and 72° C. for 1 min, before the final extension at 72° C. for 5 min. PCR products were purified using Exo nuclease and SAP before they were sequenced using BigDye (Life Technologies).

Segment sequences were aligned into two contigs (FT69 and *Oleracea*) using Sequencer 5.0 (Gene Codes Corporation) and using a minimal overlap of 20 base pairs and a minimal match of 90%). It is clear that the high MSB and MSP lines all contain the Myb28 fragment from *B. villosa* FT69 allele and control lines constitute individuals containing the *B. oleracea* allele.

The individuals used for the *B. oleracea* lines are:
GD33
breeder line 560216
breeder ID field number 2153.

The individuals used that contain the *B. villosa* FT69 allele are:
Breeder line 560526 (MSP)
Breeder line 580333 (MSB)
Breeder line BRM 51-1162 (MSP)
Breeder line BRM51-1210 (MSP).

The individuals used to identify the *B. oleracea* allele were randomly chosen from breeding material.

By comparing these sequence alignments, polymorphisms were discovered that can be used for marker based selection to select for the Myb28 allele of choice (see FIG. 1).

A total of 26 polymorphisms (e.g. single feature polymorphisms (SFPs)—of which there are 16 SNPs and 10 indels) are detected in a sequence with a total length of 2202 bp. These are shown in FIG. 1 which shows an alignment between a consensus sequence of the Myb28 locus for broccoli, with an increased level of glucosinolate, e.g. *B. villosa*, (FT69) and a consensus sequence of the Myb28 locus for broccoli, which does not have an increased level of glucosinolate, e.g. *B. oleracea*, (Oleracea). These SFPs are indicative of *B. villosa* introgression.

FIG. 2a shows SEQ ID NO: 1; a sequence of a nucleic acid fragment comprising the Myb28 locus from *Brassica oleracea* (broccoli) which does not have increased glucosinolate levels. The SFPs (including both SNPs and indels, e.g. nucleotides that can be deleted) are shaded. The nucleotides between which an SFP (indel insertion) may be inserted are underlined.

FIG. 2b shows SEQ ID NO: 2; a sequence of a nucleic acid fragment comprising the Myb28 locus from *Brassica oleracea* (broccoli) which does not have increased glucosinolate levels. The SFPs (including both SNPs and indels, e.g. nucleotides that can be deleted) are shaded. Fragments in brackets < > (and lower case nucleotides) correspond to SFPs (indels, that are insertions) in the *Brassica oleracea* sequence which insertions are found in high glucosinolate broccoli (e.g. *Brassica villosa*).

The polymorphisms detected are:

a. single nucleotide polymorphisms (SNPs) at a position corresponding to nucleotide 83, 136, 226, 563, 610, 830, 995, 1116, 1513, 1577, 1606, 1620, 1825, 1863, 1877 or 2026 of SEQ ID NO: 1, and b. polymorphisms in the number of nucleotides present between nucleotides 323 and 332, between nucleotides 521 and 524, between nucleotides 783 and 786, between nucleotides and 909 and 914, between nucleotides 1365 and 1369, between 1811 and 1821, or between nucleotides 2046 and 2056 of SEQ ID NO: 1, and c. polymorphisms in the number of nucleotides present between nucleotides 836 and 837, between nucleotides 867 and 868, or between nucleotides 943 and 944 of SEQ ID NO: 1.

Example 3

Validation of New Marker

A TaqMan assay (NBOLI009111370) was designed based on one of the sequence polymorphisms identified in Example 2.

NBOLI009111370 sequence (SEQ ID NO: 29):
GACCACCTAAAGACAAGAATAGTGAAAGAGATAAGATGGAAGACCAAA

GTTAATCAAATTTATTTTGAAGCTTTT[C/T]TATGGAATAGAGACTA

AAATGATGTGTGCTATTGCAATTTTTAGTCACATATTGCTAATCAAAC

ACATATTTTGCATCAGAGAATTGTCAAATACATGAAAAAAATAAAGAA

TAATTTTT

Forward primer (SEQ ID NO: 30):
GTGAAAGAGATAAGATGGAAGACCAAAGT

Reverse primer (SEQ ID NO: 31):
GTGACTAAAAATTGCAATAGCACACATCA

Vic probe (SEQ ID NO: 32):
CTATTCCATAGAAAAGC

Fam probe (SEQ ID NO: 33):
CTATTCCATAAAAAAGC

Load plates with 20 ng DNA template in 5 uL volume. Add 10 uL master mix (2 parts each of 1× PCR mix, 0.437 uL water, 2.5 uL Q PCR (ROX) mix, 0.063 uL assay mix, 2 uL primers at 5 ng/uL) to each well for a final volume of 15 uL.

PCR conditions are as follows: 50° C. for 2 min followed by 95° C. for 2 min then 40 cycles of 95° C. for 15 sec, 60° C. for 1 min.

Figure 6:
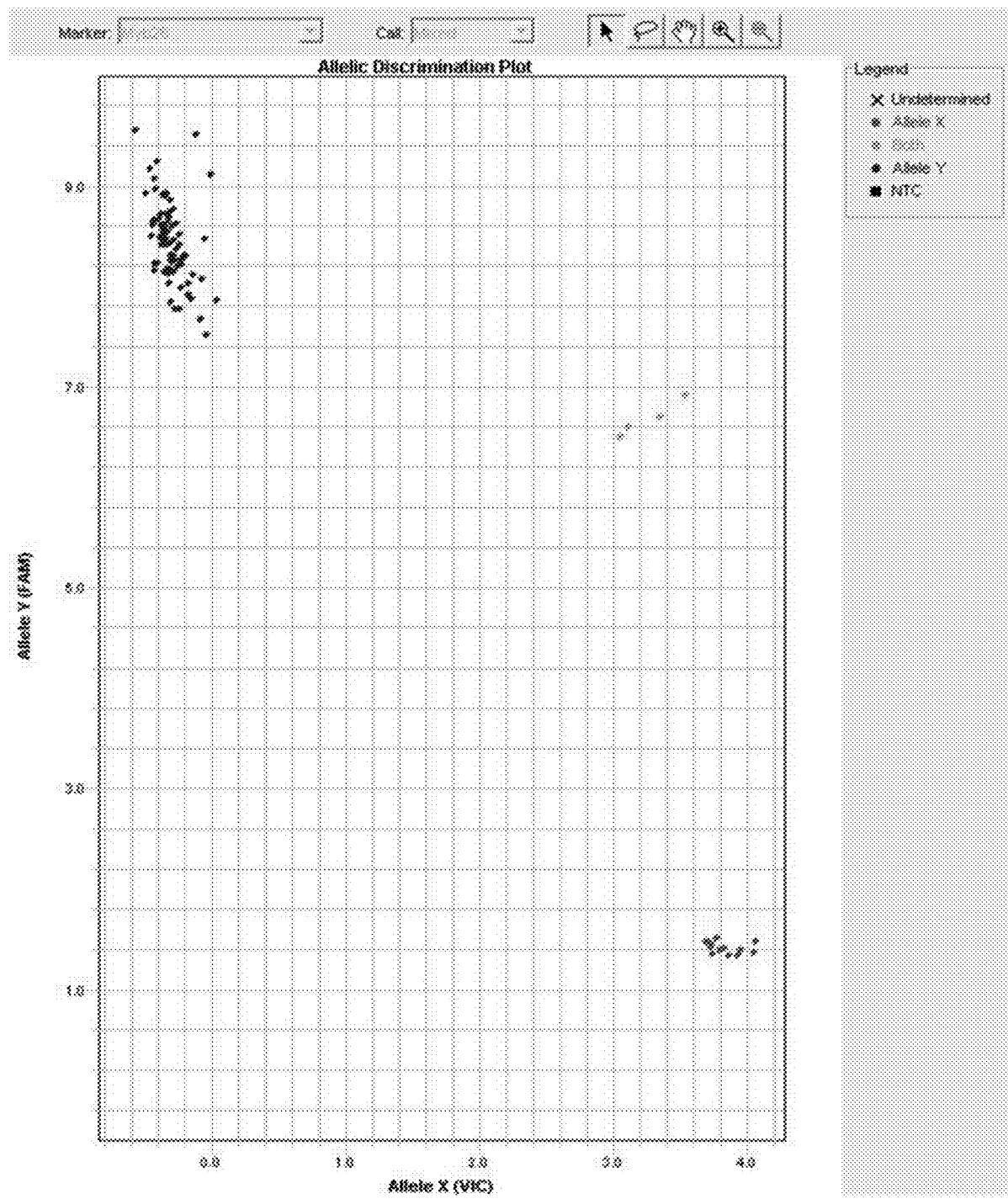
FIG. 6 shows data from a TaqMan (TM) assay designed for Myb28 in *Brassica* that validates marker effectiveness in tracking the phenotype in a germplasm panel.

This Taqman assay was run on a representative germplasm panel of 102 lines (FIG. 6). Based on the expected presence of the *B. villosa* introgression, it was determined that this marker is 100% predictive of the high glucosinolate phenotype based on the presence of the *B. villosa* allele.

Example 4

Development of New Markers

The conserved sequences (the sequence in between the SFPs) between the FT69 allele and *B. oleracea* allele have been determined and can be used for primer design and genome walking as described by Siebert et al., (1995) (An improved PCR method for walking in uncloned genomic DNA. *Nucleic Acids Res.* 23: 1087-1088) for sequence and polymorphism determination outside of the Myb28 coding region. Additional polymorphisms determined from this method of genome walking will be additionally useful for tracking the high glucosinolate trait, due to their close physical proximity and genetic linkage to the other markers described herein. These markers may be within 1, 3, 5, or 10 cM to Myb28 and may provide additional marker assays useful for tracking the high glucosinolate phenotype.

Therefore in one embodiment, the present invention provides an isolated nucleic acid comprising a sequence of at least 18 contiguous nucleotides that are conserved between SEQ ID NO: 1 and SEQ ID NO: 24 when aligned. The conserved sequences are used to prepare an isolated nucleic acid comprising a sequence of at least 18 contiguous nucleotides of SEQ ID NO: 1, wherein the sequence is not present within SEQ ID NO: 24. Alternatively the conserved sequences are used to prepare an isolated nucleic acid comprising a sequence of at least 18 contiguous nucleotides of SEQ ID NO: 24, wherein the sequence is not present within SEQ ID NO: 1.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A *Brassica oleracea* plant or a part thereof having Myb28-mediated increased glucosinolate levels, produced by a method which comprises selecting at least a first *Brassica oleracea* plant comprising a first polymorphism at the Myb28 locus that is genetically linked to increased glucosinolate levels, wherein said Myb28 locus is from *Brassica villosa*, wherein said first *Brassica oleracea* plant is selected based on the presence of said polymorphism, and wherein said first polymorphism comprises a single nucleotide polymorphism (SNP) at a position corresponding to position 1116 of SEQ ID NO: 1.

2. The plant or part thereof according to claim 1, wherein the method comprises the steps of: (a) crossing a *Brassica oleracea* plant comprising a Myb28 locus from *Brassica villosa* and having an increased glucosinolate level with a second *Brassica oleracea* plant; and (b) selecting at least a first progeny *Brassica oleracea* plant comprising a polymorphism at the Myb28 locus that is genetically linked to increasing glucosinolate levels.

3. The plant or part thereof according to claim 1, wherein:
(a) the step of selecting comprises PCR or DNA hybridization;
(b) the polymorphism is detected by a screening method comprising use of an oligonucleotide comprising a sequence selected from the group consisting of: SEQ ID NO: 3, SEQ ID NO: 30 and SEQ ID NO: 31;
(c) the selecting comprises detecting a co-dominant genetic marker;
(d) the plant is transformed with a myb28 gene comprising SEQ ID NO: 1 except for a single nucleotide polymorphism (SNP) at a position corresponding to position 1116 of SEQ ID NO: 1 and at least one other polymorphism selected from the group consisting of:
   i) a single nucleotide polymorphism (SNP) at a position corresponding to nucleotide 83, 136, 226, 563, 610, 830, 995, 1513, 1577, 1606, 1620, 1825, 1863, 1877 or 2026 of SEQ ID NO: 1, or
   ii) a polymorphism in the number of nucleotides present between nucleotides 323 and 332, between nucleotides 521 and 524, between nucleotides 783 and 786, between nucleotides 909 and 914, between nucleotides 1365 and 1369, between 1811 and 1821, or between nucleotides 2046 and 2056 of SEQ ID NO: 1, or
   iii) a polymorphism in the number of nucleotides present between nucleotides 836 and 837, between nucleotides 867 and 868, or between nucleotides 943 and 944 of SEQ ID NO: 1;
(e) the *Brassica oleracea* plant comprises 4-methylsulphinylbutyl glucosinolate (MSB) in an amount of at least 10 micromol/g dry weight; or
(f) the plant further comprises a polymorphism at least one of:
   ii) a single nucleotide polymorphism (SNP) at a position corresponding to nucleotide 83, 136, 226, 563, 610, 830, 995, 1513, 1577, 1606, 1620, 1825, 1863, 1877 or 2026 of SEQ ID NO: 1, or
   ii) a polymorphism in the number of nucleotides present between nucleotides 323 and 332, between nucleotides 521 and 524, between nucleotides 783 and 786, between nucleotides 909 and 914, between nucleotides 1365 and 1369, between 1811 and 1821, or between nucleotides 2046 and 2056 of SEQ ID NO: 1, or
   iii) a polymorphism in the number of nucleotides present between nucleotides 836 and 837, between nucleotides 867 and 868, or between nucleotides 943 and 944 of SEQ ID NO: 1.

4. The plant or part thereof according to claim 2, wherein selecting the first progeny further comprises selecting the progeny based on the presence of one or more genetic markers from the second *Brassica oleracea* plant genetically linked to at least a first additional trait.

5. The plant or part thereof according to claim 4, wherein the additional trait is selected from the group consisting of: yield, disease resistance, emergence vigor, vegetative vigor, stress tolerance, plant height, inflorescence quality, inflorescence diameter, inflorescence weight, inflorescence size, inflorescence shape, inflorescence colour, and number of days to flowering.

6. The plant or part thereof according to claim 1, wherein the plant comprises a second polymorphism at the Myb28 locus, wherein said polymorphism (a) comprises at least one of a single nucleotide polymorphism (SNP) at a position corresponding to nucleotide 83, 136, 226, 563, 610, 830, 995, 1513, 1577, 1606, 1620, 1825, 1863, 1877 or 2026 of SEQ ID NO: 1 or combinations thereof; (b) comprises a deletion of one or more of the nucleotides present between nucleotides 323 and 332, between nucleotides 521 and 524, between nucleotides 783 and 786, between nucleotides 909 and 914, between nucleotides 1365 and 1369, between 1811 and 1821, or between nucleotides 2046 and 2056 of SEQ ID NO: 1; (c) comprises a deletion of all of the nucleotides present between nucleotides 323 and 332, between nucleotides 521 and 524, between nucleotides 783 and 786, between nucleotides 909 and 914, between nucleotides 1365 and 1369, between 1811 and 1821, or between nucleotides 2046 and 2056 of SEQ ID NO: 1; (d) comprises a deletion of at least one nucleotide at a position corresponding to nucleotide 324, 325, 326, 327, 328, 329, 330, 331, 522, 523, 784, 785, 910, 911, 912, 913, 1366, 1367, 1368, 1812, 1813, 1814, 1815, 1816, 1817, 1818, 1819, 1820, 2047, 2048, 2049, 2050, 2051, 2052, 2053, 2054, or 2055 of SEQ ID NO: 1; (e) comprises a deletion of the nucleotides at the following positions: 324-331, 522-523, 784-785, 910-913, 1366-1368, 1812-1820 or 2047-2055 of SEQ ID NO: 1 or combinations thereof; or (f) comprises an insertion of one or more nucleotides between the nucleotides 836 and 837, 867 and 868, or 943 and 944 of SEQ ID NO: 1.

7. The plant or part thereof according to claim 6, wherein (a) the insertion between the nucleotides 836 and 837 is of two nucleotides; (b) the insertion between the nucleotides 836 and 837 is of TT, (c) the insertion between the nucleotides 867 and 868 is of one nucleotide, (d) the insertion between the nucleotides 867 and 868 is A, (e) the insertion between the nucleotides 943 and 944 is 13 nucleotides or up to 13 nucleotides, or (f) the insertion between the nucleotides 943 and 944 is TATTAAAAAAGTA.

8. The plant or part thereof according to claim 2, the method further comprising the step of: (c) crossing the progeny plant with itself or a third plant to produce a progeny plant of a subsequent generation.

9. The plant or part thereof according to claim 8, wherein the method further comprising the steps of: (d) crossing the progeny plant of a subsequent generation with itself or a second plant; and (e) repeating steps (c) and (d) for an additional 3-10 generations to produce an inbred *Brassica oleracea* plant comprising an increased level of glucosinolate, wherein the progeny plant of at least one subsequent generation is screened for the presence of a polymorphism at the Myb28 locus genetically linked to glucosinolate production.

10. The plant or part thereof according to claim 9, wherein:
(a) said progeny plant of a subsequent generation is selected for crossing based on the presence of glucosinolates and a desired trait;
(b) the progeny plant of a subsequent generation is selected at each generation for crossing based on the presence of an increased glucosinolate level and the desired trait; or
(c) step (e) is repeated with sufficient inbreeding to obtain an inbred *Brassica oleracea* plant that comprises an increased glucosinolate trait and otherwise comprises the agronomic traits of the second *Brassica oleracea* plant.

11. The plant or part thereof according to claim 6, wherein the polymorphism is one which is within 5 cM of said polymorphism.

12. The plant or part thereof according to claim 7, wherein the plant is transformed with a myb28 gene comprising SEQ ID NO: 24 or a sequence which has a least 97% identity with SEQ ID NO: 24.

13. A seed that produces the plant of claim 1.

14. The plant or part thereof according to claim 3, wherein the step of selecting comprises PCR or DNA hybridization.

15. The plant or part thereof according to claim 3, wherein the polymorphism is detected by a screening method comprising use of an oligonucleotide comprising a sequence selected from the group consisting of: SEQ ID NO: 3, SEQ ID NO: 30 and SEQ ID NO: 31.

16. The plant or part thereof according to claim 3, wherein the selecting comprises detecting a co-dominant genetic marker.

17. The plant or part thereof according to claim 3, wherein the plant is transformed with a myb28 gene comprising SEQ ID NO: 1 except for a single nucleotide polymorphism (SNP) at a position corresponding to position 1116 of SEQ ID NO: 1 and at least one other polymorphism selected from the group consisting of:
  i) a single nucleotide polymorphism (SNP) at a position corresponding to nucleotide 83, 136, 226, 563, 610, 830, 995, 1513, 1577, 1606, 1620, 1825, 1863, 1877 or 2026 of SEQ ID NO: 1, or
  ii) a polymorphism in the number of nucleotides present between nucleotides 323 and 332, between nucleotides 521 and 524, between nucleotides 783 and 786, between nucleotides 909 and 914, between nucleotides 1365 and 1369, between 1811 and 1821, or between nucleotides 2046 and 2056 of SEQ ID NO: 1, or
  iii) a polymorphism in the number of nucleotides present between nucleotides 836 and 837, between nucleotides 867 and 868, or between nucleotides 943 and 944 of SEQ ID NO: 1.

18. The plant or part thereof according to claim 3, wherein the *Brassica oleracea* plant comprises 4-methylsulphinyl-butyl glucosinolate (MSB) in an amount of at least 10 micromol/g dry weight.

19. The plant or part thereof according to claim 3, wherein the plant further comprises a polymorphism at least one of:
  i) a single nucleotide polymorphism (SNP) at a position corresponding to nucleotide 83, 136, 226, 563, 610, 830, 995, 1513, 1577, 1606, 1620, 1825, 1863, 1877 or 2026 of SEQ ID NO: 1, or
  ii) a polymorphism in the number of nucleotides present between nucleotides 323 and 332, between nucleotides 521 and 524, between nucleotides 783 and 786, between nucleotides 909 and 914, between nucleotides 1365 and 1369, between 1811 and 1821, or between nucleotides 2046 and 2056 of SEQ ID NO: 1, or
  iii) a polymorphism in the number of nucleotides present between nucleotides 836 and 837, between nucleotides 867 and 868, or between nucleotides 943 and 944 of SEQ ID NO: 1.

20. The plant or part thereof according to claim 12, wherein the plant is transformed with a myb28 gene comprising a sequence which has at least 97% identity with SEQ ID NO: 24.

21. The plant or part thereof according to claim 12, wherein the plant is transformed with a myb28 gene comprising SEQ ID NO:24.

* * * * *

SEQUENCE LISTING

<160> NUMBER OF SEQ ID NOS: 35

<210> SEQ ID NO 1
<211> LENGTH: 2186
<212> TYPE: DNA
<213> ORGANISM: Brassica oleracea

<400> SEQUENCE: 1

```
gaaaatcaca gttcacgcct cttactccat gagcttctct attctcatcc tagtgttata      60
atcttgcaaa cacatataga aagcaaggtt tggagtgtac gagaaaaaca tgaaaacacc     120
tagaagctct gtgggtgaga cccaagagcg tttctcgatt agtttcatat acagatgcat     180
cagagttctc atcaaccgat ctacttcttt cttatcttat tagaagaaaa aaatcctatc     240
aaaatttact ttcctgcaag tatattttt c tttacatttt cattttcttg agtgttattt     300
gagtgaagtt atattaaaat attgtaatag agttcatata tatcgaaaat gtcaagaaag     360
ccatgttgtg tcggagaagg gctgaagaaa ggggcatgga ccaccgagga agataagaaa     420
ctcatctctt acatccatga acatggagaa ggaggctggc gcgacattcc tcaaaaagct     480
ggttaatatc tattatatat ttttggtaa attttaaaa catatatatg tttgtttggt     540
atttgatgta tgaaagtttt atgttgaata tggtgttta ctaggrttga aaaggtgtgg     600
aaagagttgt agactgcgat ggactaacta cctaaaacct gagatcaaaa gaggcgagtt     660
tagttcagag gaggaacaga ttatcatcat gctccatgct gctcgtggca acaagtacgt     720
ttattttaga ccaaaaaaaa acaagtacgt ttattttaa caaaaaggac gattatatat     780
ttttatgtgt gtatggatcc tccagtgatc atcattctag ttttctcttt tttttatac     840 cgcaaacaaa tttcattagt aaaaaaatta aaattccaaa gtcaatattc aaaaacacag     900
tgttatatat ataatcctat atatgtcata tattaaaaaa gtacaacatg agaaatgaat     960
ttaagtatgc ttctaaagcg aagttttact tcccgaaaaa ttattcttta tttttttcat    1020
gtatttgaca attctctgat gcaaaatatg tgtttgatta gcaatatgtg actaaaaatt    1080
gcaatagcac acatcatttt agtctctatt ccataaaaaa gcttcaaaat aaatttgatt    1140
aactttggtc ttccatctta tctctttcac tattcttgtc tttaggtggt cggtcatagc    1200 kagacatttta cctagaagaa cmgacaatga gatcaagaac tactggaaca cacatctcaa    1260
gaaacgtttg atcgaacagg gtactgatcc cgtgactcac aagccactag cttctaatac    1320
aaaccctact gtacctgaga atttgcattc cctagatgca tctagtaatt ccgacaagca    1380
atactcccgg tcaagctcaa tgccttccat gtcttgtact ccttcctccg gtttcaacac    1440
ggttttcgag aataccagca agatgggac accagttcgt gaggacgatt ccttgagtcg    1500
caagaaacgt tttaagaaat caagttctac atcaaggctt ttgaacaaag ttgcggctaa    1560
ggccacttcc atgaaagaag ctttgtctgc ttccatggaa ggtagtttga atgctaatac    1620
aagcttttcc aatggctact ctgagcagat tctcaatgaa gatgatagtt ctaatgcatc    1680
cctcataaac actctcgccg agttcgatcc cttcctccaa acaacgtttt accctgagaa    1740
tgagatgaat actacttctg atctcggtat agatcaggac tacttctcac attttctcga    1800
aaatttcggc agagatgatg accacaatga ggagcactac atgaatcata actatggtca    1860
tgatcttctt atgtccgatg tgtcccaaga agtctcatca actagcgttg atgatcaaga    1920
caatactaat gagggttggt caaattatct tcttgaccat gctgatttta tacatgacat    1980
ggattctgat tccctcggaa agcatctcat atgaatcttc gtgcccaagc agaaaggttt    2040
caaacttttg aaacttgtca gaacaagaag ttatgtatgt attctattat atggattgtt    2100
```

| | |
|---|---|
| tagtatatgt ccaagatcat ggttgttagt cccaagttta gggtttgtat aatatacaat | 2160 |
| aagggacgtt atcttataaa acgagg | 2186 |

<210> SEQ ID NO 2
<211> LENGTH: 2202
<212> TYPE: DNA
<213> ORGANISM: Brassica oleracea

<400> SEQUENCE: 2

| | |
|---|---|
| gaaaatcaca gttcacgcct cttactccat gagcttctct attctcatcc tagtgttata | 60 |
| atcttgcaaa cacatataga aagcaaggtt tggagtgtac gagaaaaaca tgaaaacacc | 120 |
| tagaagctct gtgggtgaga cccaagagcg tttctcgatt agtttcatat acagatgcat | 180 |
| cagagttctc atcaaccgat ctacttcttt cttatcttat tagaagaaaa aaatcctatc | 240 |
| aaaatttact ttcctgcaag tatattttc tttacatttt cattttcttg agtgttattt | 300 |
| gagtgaagtt atattaaaat attgtaatag agttcatata tatcgaaaat gtcaagaaag | 360 |
| ccatgttgtg tcggagaagg gctgaagaaa ggggcatgga ccaccgagga agataagaaa | 420 |
| ctcatctctt acatccatga acatggagaa ggaggctggc gcgacattcc tcaaaaagct | 480 |
| ggttaatatc tattatatat tttttggtaa attttaaaa catatatatg tttgtttggt | 540 |
| atttgatgta tgaaagtttt atgttgaata tggtgtttta ctaggrttga aaaggtgtgg | 600 |
| aaagagttgt agactgcgat ggactaacta cctaaaacct gagatcaaaa gaggcgagtt | 660 |
| tagttcagag gaggaacaga ttatcatcat gctccatgct gctcgtggca acaagtacgt | 720 |
| ttattttaga ccaaaaaaaa acaagtacgt ttattttaa caaaaaggac gattatatat | 780 |
| ttttatgtgt gtatggatcc tccagtgatc atcattctag ttttctcttt ttttttttat | 840 |
| accgcaaaca aatttcatta gtaaaaaaaa ttaaaattcc aaagtcaata ttcaaaaaca | 900 |
| cagtgttata tatataatcc tatatatgtc atatattaaa aaagtatatt aaaaaagtac | 960 |
| aacatgagaa atgaatttaa gtatgcttct aaagcgaagt tttacttccc gaaaaattat | 1020 |
| tcttttatttt tttcatgtat ttgacaattc tctgatgcaa aatatgtgtt tgattagcaa | 1080 |
| tatgtgacta aaaattgcaa tagcacacat cattttagtc tctattccat aaaaaagctt | 1140 |
| caaaataaat ttgattaact ttggtcttcc atcttatctc tttcactatt cttgtctta | 1200 |
| ggtggtcggt catagckaga catttaccta gaagaacmga caatgagatc aagaactact | 1260 |
| ggaacacaca tctcaagaaa cgtttgatcg aacagggtac tgatcccgtg actcacaagc | 1320 |
| cactagcttc taatacaaac cctactgtac ctgagaattt gcattcccta gatgcatcta | 1380 |
| gtaattccga caagcaatac tcccggtcaa gctcaatgcc ttccatgtct tgtactcctt | 1440 |
| cctccggttt caacacggtt ttcgagaata ccagcaaaga tgggacacca gttcgtgagg | 1500 |
| acgattcctt gagtcgcaag aaacgtttta agaaatcaag ttctacatca aggcttttga | 1560 |
| acaaagttgc ggctaaggcc acttccatga agaagctttt gtctgcttcc atggaaggta | 1620 |
| gtttgaatgc taatacaagc ttttccaatg gctactctga gcagattctc aatgaagatg | 1680 |
| atagttctaa tgcatccctc ataaacactc tcgccgagtt cgatcccttc ctccaaacaa | 1740 |
| cgttttaccc tgaatgagag atgaatacta cttctgatct cggtatagat caggactact | 1800 |
| tctcacattt tctcgaaaat ttcggcagag atgatgacca caatgaggag cactacatga | 1860 |
| atcataacta tggtcatgat cttcttatgt ccgatgtgtc ccaagaagtc tcatcaacta | 1920 |
| gcgttgatga tcaagacaat actaatgagg gttggtcaaa ttatcttctt gaccatgctg | 1980 |

```
atttttataca tgacatggat tctgattccc tcggaaagca tctcatatga atcttcgtgc    2040
ccaagcagaa aggtttcaaa cttttgaaac ttgtcagaac aagaagttat gtatgtattc    2100
tattatatgg attgtttagt atatgtccaa gatcatggtt gttagtccca agtttagggt    2160
ttgtataata tacaataagg gacgttatct tataaaacga gg                       2202
```

<210> SEQ ID NO 3
<211> LENGTH: 20
<212> TYPE: DNA
<213> ORGANISM: Artificial Sequence
<220> FEATURE:
<223> OTHER INFORMATION: primer OD00876

<400> SEQUENCE: 3

```
tcacgaacat ggagaaggtg                                                  20
```

<210> SEQ ID NO 4
<211> LENGTH: 20
<212> TYPE: DNA
<213> ORGANISM: Artificial Sequence
<220> FEATURE:
<223> OTHER INFORMATION: primer OD00877

<400> SEQUENCE: 4

```
tgagcttgac cgggagtatc                                                  20
```

<210> SEQ ID NO 5
<211> LENGTH: 20
<212> TYPE: DNA
<213> ORGANISM: Artificial Sequence
<220> FEATURE:
<223> OTHER INFORMATION: primer OD00878

<400> SEQUENCE: 5

```
ctaactacct aaaacctgag                                                  20
```

<210> SEQ ID NO 6
<211> LENGTH: 19
<212> TYPE: DNA
<213> ORGANISM: Artificial Sequence
<220> FEATURE:
<223> OTHER INFORMATION: primer OD00879

<400> SEQUENCE: 6

```
ctagtggctt gtgagtcac                                                   19
```

<210> SEQ ID NO 7
<211> LENGTH: 22
<212> TYPE: DNA
<213> ORGANISM: Artificial Sequence
<220> FEATURE:
<223> OTHER INFORMATION: primer OD00880

<400> SEQUENCE: 7

```
cctcgtttta taagataacg tc                                               22
```

<210> SEQ ID NO 8
<211> LENGTH: 21
<212> TYPE: DNA
<213> ORGANISM: Artificial Sequence
<220> FEATURE:
<223> OTHER INFORMATION: primer OD00881

<400> SEQUENCE: 8

```
ctcgatatag atcaggacta c                                                21
```

```
<210> SEQ ID NO 9
<211> LENGTH: 20
<212> TYPE: DNA
<213> ORGANISM: Artificial Sequence
<220> FEATURE:
<223> OTHER INFORMATION: primer OD00882

<400> SEQUENCE: 9
gatgagactt cttgggacac                                              20

<210> SEQ ID NO 10
<211> LENGTH: 19
<212> TYPE: DNA
<213> ORGANISM: Artificial Sequence
<220> FEATURE:
<223> OTHER INFORMATION: primer OD00883

<400> SEQUENCE: 10
gaggacgatt ccttgagtc                                               19

<210> SEQ ID NO 11
<211> LENGTH: 19
<212> TYPE: DNA
<213> ORGANISM: Artificial Sequence
<220> FEATURE:
<223> OTHER INFORMATION: primer OD00884

<400> SEQUENCE: 11
accttccatg gaagcagac                                               19

<210> SEQ ID NO 12
<211> LENGTH: 22
<212> TYPE: DNA
<213> ORGANISM: artificial sequence
<220> FEATURE:
<223> OTHER INFORMATION: primer OD00885

<400> SEQUENCE: 12
tgtgtttgat tagcaatatg tg                                           22

<210> SEQ ID NO 13
<211> LENGTH: 19
<212> TYPE: DNA
<213> ORGANISM: Artificial Sequence
<220> FEATURE:
<223> OTHER INFORMATION: primer OD00886

<400> SEQUENCE: 13
agcagcatgg agcatgatg                                               19

<210> SEQ ID NO 14
<211> LENGTH: 18
<212> TYPE: DNA
<213> ORGANISM: Artificial Sequence
<220> FEATURE:
<223> OTHER INFORMATION: primer OD00887

<400> SEQUENCE: 14
tgtgtcggag aagggctg                                                18

<210> SEQ ID NO 15
<211> LENGTH: 18
<212> TYPE: DNA
<213> ORGANISM: Artificial Sequence
<220> FEATURE:
```

```
<223> OTHER INFORMATION: primer OD00888

<400> SEQUENCE: 15
ccagccacct tctccatg                                                 18

<210> SEQ ID NO 16
<211> LENGTH: 19
<212> TYPE: DNA
<213> ORGANISM: Artificial Sequence
<220> FEATURE:
<223> OTHER INFORMATION: primer OD889

<400> SEQUENCE: 16
acgcctctta ctccatgag                                                19

<210> SEQ ID NO 17
<211> LENGTH: 23
<212> TYPE: DNA
<213> ORGANISM: Artificial Sequence
<220> FEATURE:
<223> OTHER INFORMATION: primer OD0890

<400> SEQUENCE: 17
tcctatcaaa atttactttc ctg                                           23

<210> SEQ ID NO 18
<211> LENGTH: 20
<212> TYPE: DNA
<213> ORGANISM: Artificial Sequence
<220> FEATURE:
<223> OTHER INFORMATION: primer OD00891

<400> SEQUENCE: 18
cagtctgcaa ctctttccac                                               20

<210> SEQ ID NO 19
<211> LENGTH: 20
<212> TYPE: DNA
<213> ORGANISM: Artificial Sequence
<220> FEATURE:
<223> OTHER INFORMATION: primer OD00892

<400> SEQUENCE: 19
ctttaggtgg tcggtcatag                                               20

<210> SEQ ID NO 20
<211> LENGTH: 20
<212> TYPE: DNA
<213> ORGANISM: Artificial Sequence
<220> FEATURE:
<223> OTHER INFORMATION: primer OD00893

<400> SEQUENCE: 20
tcagggtaaa acgttgtttg                                               20

<210> SEQ ID NO 21
<211> LENGTH: 22
<212> TYPE: DNA
<213> ORGANISM: Artificial Sequence
<220> FEATURE:
<223> OTHER INFORMATION: primer OD00951

<400> SEQUENCE: 21
tgtatttgac aattctctga tg                                            22
```

<210> SEQ ID NO 22
<211> LENGTH: 19
<212> TYPE: DNA
<213> ORGANISM: Artificial Sequence
<220> FEATURE:
<223> OTHER INFORMATION: primer OD00952

<400> SEQUENCE: 22
ttcatggaag tggccttag                                                    19

<210> SEQ ID NO 23
<211> LENGTH: 20
<212> TYPE: DNA
<213> ORGANISM: Artificial Sequence
<220> FEATURE:
<223> OTHER INFORMATION: primer OD00953

<400> SEQUENCE: 23
cttgggacta acaaccatga                                                   20

<210> SEQ ID NO 24
<211> LENGTH: 2165
<212> TYPE: DNA
<213> ORGANISM: Brassica villosa FT69

<400> SEQUENCE: 24
gaaaatcaca gttcacgcct cttactccat gagcttctct attctcatcc tagtgttata        60
atcttgcaaa cacatataga aagcaagatt tggagtgtac gagaaaaaca tgaaaacacc       120
tagaagctct gtgggtaaga cccaagagcg tttctcgatt agtttcatat acagatgcat       180
cagagttctc atcaaccgat ctacttcttt cttatcttat tagaaaaaaa aaatcctatc       240
aaaatttact ttcctgcaag tatattttc tttacatttt cattttcttg agtgttattt        300
gagtgaagtt atattaaaat attgttcata tatatcgaaa atgtcaagaa agccatgttg       360
tgtcggagaa gggctgaaga aaggggcatg gaccaccgag gaagataaga aactcatctc       420
ttacatccat gaacatggag aaggaggctg gcgcgacatt cctcaaaaag ctggttaata       480
tctattatat attttttggt aaattttaa aacatatatg tttgtttggt atttgatgta        540
tgaaagtttt atattgaatg tggtgtttta ctaggattga aaaggtgtgg aaagagttgc       600
agactgcgat ggactaacta cctaaaacct gagatcaaaa gaggcgagtt tagttcagag       660
gaggaacaga ttatcatcat gctccatgct gctcgtggca acaagtacgt ttattttaga       720
ccaaaaaaaa acaagtacgt ttatttttaa caaaaaggac gattatatat ttttgtgtgt       780
atggatcctc cagtgatcat cattctagtt ttctcttctt tttttatac cgcaaacaaa       840 tttcattagt aaaaaaaatt aaaattccaa agtcaatatt caaaacaca gtgttatata        900 atcctatata tgtcatatat taaaaagta tattaaaaaa gtacaacatg agaaatgaat        960
ttaagtatgc ttctaaagcg aagttttact tcccaaaaaa ttattcttta tttttttcat      1020
gtatttgaca attctctgat gcaaaatatg tgtttgatta gcaatatgtg actaaaaatt      1080
gcaatagcac acatcatttt agtctctatt ccatagaaaa gcttcaaaat aaatttgatt      1140
aactttggtc ttccatctta tctctttcac tattcttgtc tttaggtggt cggtcatagc      1200
kagacattta cctagaagaa cmgacaatga gatcaagaay tactggaaca cacatctcaa      1260
gaaacgtttg atcgaacagg gtactgatcc cgtgactcac aagccactag cttctaatac      1320
aaaccctact gtacctgaga atttgcattc cctagatgca tctagttccg acaagcaata      1380
ctcccggtca agctcaatgc cttccatgtc ttgtactcct tcctccggtt tcaacacggt      1440

-continued

```
tttcgagaat accagcaaag atgggacacc agttcgtgag gacgattcct tgagtcgcaa    1500
gaaacgtttg aagaaatcaa gttctacatc aaggcttttg aacaaagttg cggctaaggc    1560
cacttccatg aaaaaagctt tgtctgcttc catggaaggt agcttgaatg ctaatataag    1620
cttttccaat ggctactctg agcagattct caatgaagat gatagttcta atgcatccct    1680
cataaacact ctcgccgagt tcgatccctt cctccaaaca acgttttacc ctgagaatga    1740
gatgaatact acttctgatc tcggtataga tcaggactac ttctcacatt ttctcgaaaa    1800
tttcggcaac cataatgagg agcactacat gaatcataac tatggtcatg gtcttcttat    1860
gtcctatgtg tcccaagaag tctcatcaac tagcgttgat gatcaagaca atactaatga    1920
gggttggtca aattatcttc ttgaccatgc tgattttata catgacatgg attctgattc    1980
cctcggaaag catctcatat gaatcttcgt gcctaagcag aaaggtttca aacttgtcag    2040
aacaagaagt tatgtatgta ttctattata tggattgttt agtatatgtc caagatcatg    2100
gttgttagtc ccaagtttag ggtttgtata atatacaata agggacgtta tcttataaaa    2160
cgagg                                                                 2165
```

<210> SEQ ID NO 25
<211> LENGTH: 13
<212> TYPE: DNA
<213> ORGANISM: Artificial Sequence
<220> FEATURE:
<223> OTHER INFORMATION: sequence for insertion between nucleotides 943
    and 944 of SEQ ID NO 1

<400> SEQUENCE: 25
tattaaaaaa gta                                                        13

<210> SEQ ID NO 26
<211> LENGTH: 22
<212> TYPE: DNA
<213> ORGANISM: Artificial Sequence
<220> FEATURE:
<223> OTHER INFORMATION: primer Myb28

<400> SEQUENCE: 26
ctcttcctct ttcctcgggt tt                                              22

<210> SEQ ID NO 27
<211> LENGTH: 23
<212> TYPE: DNA
<213> ORGANISM: Artificial Sequence
<220> FEATURE:
<223> OTHER INFORMATION: primer Myb28 Rev

<400> SEQUENCE: 27
tgcaactcaa ggaacctctc tga                                             23

<210> SEQ ID NO 28
<211> LENGTH: 25
<212> TYPE: DNA
<213> ORGANISM: Artificial Sequence
<220> FEATURE:
<223> OTHER INFORMATION: Myb28 probe

<400> SEQUENCE: 28
aacccggttt ccgagatcac cacac                                           25

<210> SEQ ID NO 29
<211> LENGTH: 196
<212> TYPE: DNA

```
<213> ORGANISM: Artificial Sequence
<220> FEATURE:
<223> OTHER INFORMATION: Taqman assay NBOLI009111370

<400> SEQUENCE: 29
gaccacctaa agacaagaat agtgaaagag ataagatgga agaccaaagt taatcaaatt      60
tattttgaag cttttytatg gaatagagac taaaatgatg tgtgctattg caattttttag   120 tcacatattg ctaatcaaac acatattttg catcagagaa ttgtcaaata catgaaaaaa    180
ataaagaata attttt                                                    196

<210> SEQ ID NO 30
<211> LENGTH: 29
<212> TYPE: DNA
<213> ORGANISM: Artificial Sequence
<220> FEATURE:
<223> OTHER INFORMATION: forward primer

<400> SEQUENCE: 30
gtgaaagaga taagatggaa gaccaaagt                                       29

<210> SEQ ID NO 31
<211> LENGTH: 29
<212> TYPE: DNA
<213> ORGANISM: Artificial Sequence
<220> FEATURE:
<223> OTHER INFORMATION: reverse primer

<400> SEQUENCE: 31
gtgactaaaa attgcaatag cacacatca                                       29

<210> SEQ ID NO 32
<211> LENGTH: 17
<212> TYPE: DNA
<213> ORGANISM: Artificial Sequence
<220> FEATURE:
<223> OTHER INFORMATION: Vic probe

<400> SEQUENCE: 32
ctattccata gaaaagc                                                    17

<210> SEQ ID NO 33
<211> LENGTH: 17
<212> TYPE: DNA
<213> ORGANISM: Artificial Sequence
<220> FEATURE:
<223> OTHER INFORMATION: Fam probe

<400> SEQUENCE: 33
ctattccata aaaaagc                                                    17

<210> SEQ ID NO 34
<211> LENGTH: 2165
<212> TYPE: DNA
<213> ORGANISM: Brassica villosa FT69

<400> SEQUENCE: 34
gaaaatcaca gttcacgcct cttactccat gagcttctct attctcatcc tagtgttata     60
atcttgcaaa cacatataga aagcaagatt tggagtgtac gagaaaaaca tgaaaacacc    120
tagaagctct gtgggtaaga cccaagagcg tttctcgatt agtttcatat acagatgcat    180
cagagttctc atcaaccgat ctacttcttt cttatccttat tagaaaaaaa aaatcctatc   240
aaaatttact ttcctgcaag tatattttc tttacatttt cattttcttg agtgttattt     300
```

```
gagtgaagtt atattaaaat attgttcata tatatcgaaa atgtcaagaa agccatgttg      360
tgtcggagaa gggctgaaga aaggggcatg gaccaccgag gaagataaga aactcatctc      420
ttacatccat gaacatggag aaggaggctg gcgcgacatt cctcaaaaag ctggttaata      480
tctattatat atttttggt aaatttttaa aacatatatg tttgtttggt atttgatgta       540
tgaaagtttt atattgaatg tggtgtttta ctaggattga aaaggtgtgg aaagagttgc      600
agactgcgat ggactaacta cctaaaacct gagatcaaaa gaggcgagtt tagttcagag      660
gaggaacaga ttatcatcat gctccatgct gctcgtggca acaagtacgt ttattttaga      720
ccaaaaaaaa acaagtacgt ttattttaa caaaaaggac gattatatat ttttgtgtgt       780
atggatcctc cagtgatcat cattctagtt ttctcttctt ttttttatac cgcaaacaaa      840
tttcattagt aaaaaaaatt aaaattccaa agtcaatatt caaaaacaca gtgttatata      900
atcctatata tgtcatatat taaaaaagta tattaaaaaa gtacaacatg agaaatgaat      960
ttaagtatgc ttctaaagcg aagttttact tcccaaaaaa ttattcttta ttttttttcat    1020 gtatttgaca attctctgat gcaaaatatg tgtttgatta gcaatatgtg actaaaaatt     1080
gcaatagcac acatcatttt agtctctatt ccatagaaaa gcttcaaaat aaatttgatt     1140
aactttggtc ttccatctta tctctttcac tattcttgtc tttaggtggt cggtcatagc     1200
kagacattta cctagaagaa cmgacaatga gatcaagaay tactggaaca cacatctcaa    1260
gaaacgtttg atcgaacagg gtactgatcc cgtgactcac aagccactag cttctaatac    1320
aaaccctact gtacctgaga atttgcattc cctagatgca tctagttccg acaagcaata    1380
ctcccggtca agctcaatgc cttccatgtc ttgtactcct cctccggtt tcaacacggt     1440 tttcgagaat accagcaaag atgggacacc agttcgtgag gacgattcct tgagtcgcaa    1500
gaaacgtttg aagaaatcaa gttctacatc aaggcttttg aacaaagttg cggctaaggc    1560
cacttccatg aaaaaagctt tgtctgcttc catggaaggt agcttgaatg ctaatataag    1620
cttttccaat ggctactctg agcagattct caatgaagat gatagttcta atgcatccct    1680
cataaacact ctcgccgagt tcgatcccct cctccaaaca acgttttacc ctgagaatga    1740
gatgaatact acttctgatc tcggtataga tcaggactac ttctcacatt ttctcgaaaa    1800
tttcggcaac cataatgagg agcactacag gaatcataac tatggtcatg gtcttcttat    1860
gtcctatgtg tcccaagaag tctcatcaac tagcgttgat gatcaagaca atactaatga    1920
gggttggtca aattatcttc ttgaccatgc tgattttata catgacatgg attctgattc    1980
cctcggaaag catctcatat gaatcttcgt gcctaagcag aaaggtttca aacttgtcag    2040
aacaagaagt tatgtatgta ttctattata tggattgttt agtatatgtc caagatcatg    2100
gttgttagtc ccaagtttag ggtttgtata atatacaata agggacgtta tcttataaaa    2160
cgagg                                                                 2165
```

<210> SEQ ID NO 35
<211> LENGTH: 2186
<212> TYPE: DNA
<213> ORGANISM: Brassica oleracea

<400> SEQUENCE: 35

```
gaaaatcaca gttcacgcct cttactccat gagcttctct attctcatcc tagtgttata       60
atcttgcaaa cacatataga aagcaaggtt tggagtgtac gagaaaaaca tgaaaacacc     120
tagaagctct gtgggtgaga cccaagagcg tttctcgatt agtttcatat acagatgcat     180
```

```
cagagttctc atcaaccgat ctacttcttt cttatcttat tagaagaaaa aaatcctatc    240
aaaatttact ttcctgcaag tatattttc  tttacatttt cattttcttg agtgttattt    300
gagtgaagtt atattaaaat attgtaatag agttcatata tatcgaaaat gtcaagaaag    360
ccatgttgtg tcggagaagg gctgaagaaa ggggcatgga ccaccgagga agataagaaa    420
ctcatctctt acatccatga acatggagaa ggaggctggc gcgacattcc tcaaaaagct    480
ggttaatatc tattatatat tttttggtaa attttaaaa  catatatatg tttgtttggt    540
atttgatgta tgaaagtttt atgttgaata tggtgtttta ctaggrttga aaaggtgtgg    600
aaagagttgt agactgcgat ggactaacta cctaaaacct gagatcaaaa gaggcgagtt    660
tagttcagag gaggaacaga ttatcatcat gctccatgct gctcgtggca acaagtacgt    720
ttatttaga  ccaaaaaaaa acaagtacgt ttatttttaa caaaaaggac gattatatat    780
ttttatgtgt gtatggatcc tccagtgatc atcattctag ttttctcttt tttttatac    840
cgcaaacaaa tttcattagt aaaaaaatta aaattccaaa gtcaatattc aaaaacacag    900
tgttatatat ataatcctat atatgtcata tattaaaaaa gtacaacatg agaaatgaat    960
ttaagtatgc ttctaaagcg aagtttact  tcccgaaaaa ttattcttta ttttttttcat  1020
gtatttgaca attctctgat gcaaaatatg tgtttgatta gcaatatgtg actaaaaatt   1080
gcaatagcac acatcatttt agtctctatt ccataaaaaa gcttcaaaat aaatttgatt   1140
aactttggtc ttccatctta tctctttcac tattcttgtc tttaggtggt cggtcatagc   1200
kagacattta cctagaagaa cmgacaatga gatcaagaac tactggaaca cacatctcaa   1260
gaaacgtttg atcgaacagg gtactgatcc cgtgactcac aagccactag cttctaatac   1320
aaaccctact gtacctgaga atttgcattc cctagatgca tctagtaatt ccgacaagca   1380
atactcccgg tcaagctcaa tgccttccat gtcttgtact ccttcctccg gtttcaacac   1440
ggttttcgag aataccagca aagatgggac accagttcgt gaggacgatt ccttgagtcg   1500
caagaaacgt tttaagaaat caagttctac atcaaggctt ttgaacaaag ttgcggctaa   1560
ggccacttcc atgaaagaag ctttgtctgc ttccatggaa ggtagtttga atgctaatac   1620
aagcttttcc aatggctact ctgagcagat tctcaatgaa gatgatagtt ctaatgcatc   1680
cctcataaac actctcgccg agttcgatcc cttcctccaa acaacgtttt accctgagaa   1740
tgagatgaat actacttctg atctcggtat agatcaggac tacttctcac attttctcga   1800
aaatttcggc agagatgatg accacaatga ggagcactac atgaatcata actatggtca   1860
tgatcttctt atgtccgatg tgtcccaaga agtctcatca actagcgttg atgatcaaga   1920
caatactaat gagggttggt caaattatct tcttgaccat gctgattta  tacatgacat   1980
ggattctgat tccctcggaa agcatctcat atgaatcttc gtgcccaagc agaaaggttt   2040
caaacttttg aaacttgtca gaacaagaag ttatgtatgt attctattat atggattgtt   2100
tagtatatgt ccaagatcat ggttgttagt cccaagttta gggtttgtat aatatacaat   2160
aagggacgtt atcttataaa acgagg                                        2186
```